Figure 1:
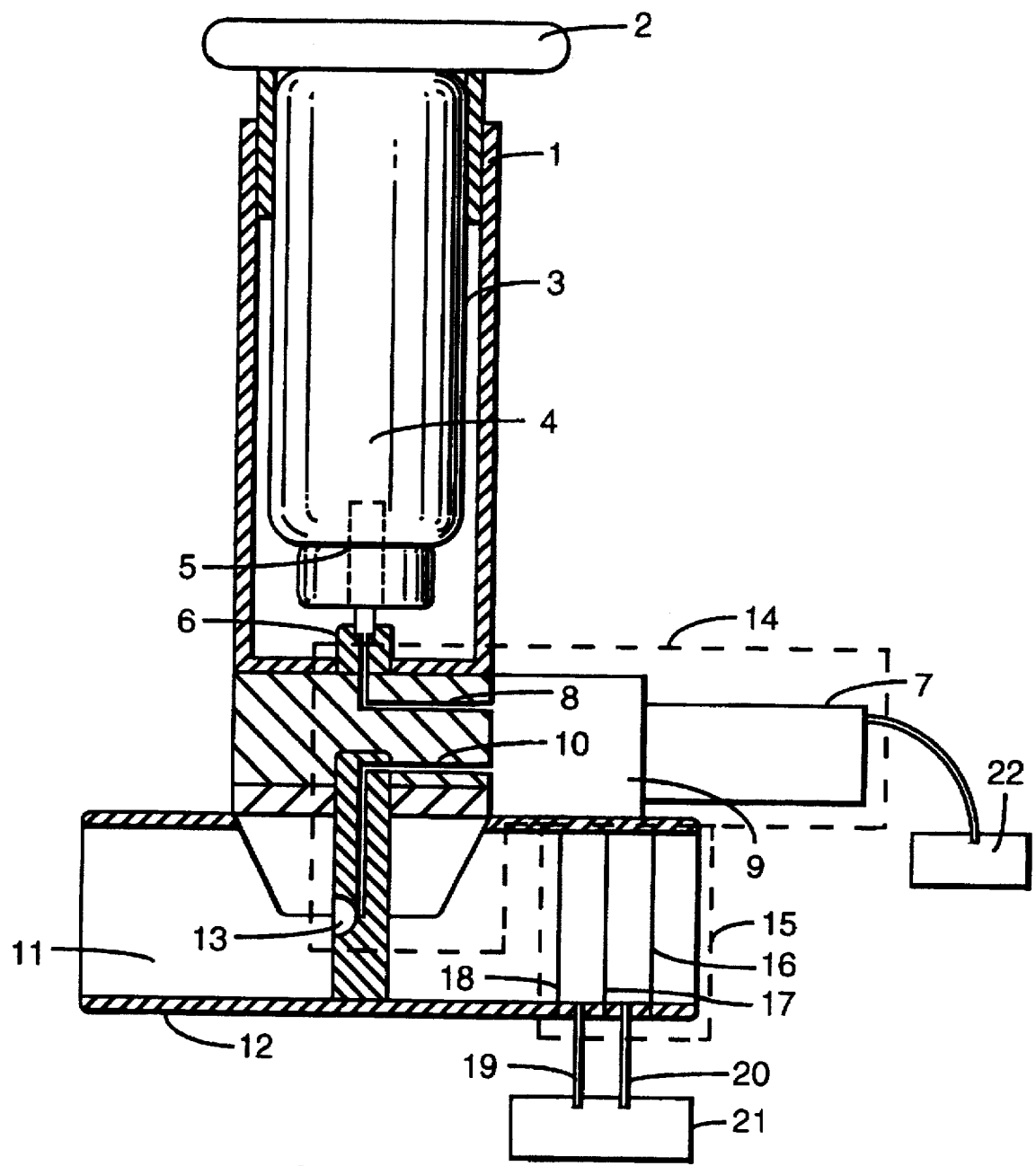

United States Patent [19]

Rubsamen et al.

[11] Patent Number: 5,694,919

[45] Date of Patent: *Dec. 9, 1997

[54] LOCKOUT DEVICE FOR CONTROLLED RELEASE OF DRUG FROM PATIENT-ACTIVATED DISPENSER

[75] Inventors: Reid M. Rubsamen, Berkeley; Lester J. Lloyd, Orinda; Eric T. Johansson, Dublin, all of Calif.

[73] Assignee: Aradigm Corporation, Hayward, Calif.

[*] Notice: The term of this patent shall not extend beyond the expiration date of Pat. No. 5,507,277.

[21] Appl. No.: 549,017

[22] Filed: Oct. 27, 1995

Related U.S. Application Data

[63] Continuation-in-part of Ser. No. 331,065, Oct. 28, 1994, Pat. No. 5,507,277, which is a continuation-in-part of Ser. No. 11,289, Jan. 29, 1993, abandoned.

[51] Int. Cl.$^6$ .................................................. A61M 11/00
[52] U.S. Cl. ................................ 128/200.14; 128/200.23; 128/202.22; 128/204.21; 128/204.23; 128/205.23
[58] Field of Search ........................ 128/200.14, 200.23, 128/204.21, 204.23, 205.23, 202.22

[56] References Cited

U.S. PATENT DOCUMENTS

| | | | |
|---|---|---|---|
| 3,812,854 | 5/1974 | Michaels et al. | 128/200.16 |
| 3,991,304 | 11/1976 | Hillsman | 128/725 |
| 4,604,847 | 8/1986 | Moulding, Jr. et al. | 53/75 |
| 4,686,231 | 8/1987 | Bender et al. | 514/333 |
| 4,984,158 | 1/1991 | Hillsman | 128/725 |
| 5,020,527 | 6/1991 | Dessertine | 128/200.23 |
| 5,293,865 | 3/1994 | Altner et al. | 128/203.12 |
| 5,363,842 | 11/1994 | Mishelevich et al. | 128/200.23 |
| 5,497,944 | 3/1996 | Weston et al. | 239/321 |
| 5,507,277 | 4/1996 | Rubsamen et al. | 128/200.14 |

FOREIGN PATENT DOCUMENTS

| | | |
|---|---|---|
| 0 232 235 A2 | 8/1987 | European Pat. Off. . |

OTHER PUBLICATIONS

Camp, J.P., "Patient-Controlled Analgesia", 1991, AFP Clinical Pharmacology, 44:2145–2150.

(List continued on next page.)

*Primary Examiner*—Aaron J. Lewis
*Attorney, Agent, or Firm*—Karl Bozicevic

[57] ABSTRACT

A method of controlling access to a drug in an aerosol drug delivery device by an electronic lock and key means is disclosed. Access is limited to the intended user by providing the intended user with a uniquely coded, machine readable key means that matches the unique code of the lock means. Contacting matching lock and key means signals a controlling means to allow use of the device. Specifically, the method is applied to a method of pain control provided by the intrapulmonary delivery of a pharmaceutically active pain relief formulation. The formulation is automatically released from a hand-held, self-contained, portable device comprised of a means for automatically releasing a measured amount of drug into the inspiratory flow path of a patient in response to information obtained from a means for measuring and separately determining inspiratory flow rate and inspiratory volume of a patient. Reproducible dosing is obtained by providing for automatic release in response to a separately measured inspiratory rate and inspiratory volume. To obtain repeatability in dosing the narcotic formulation is repeatedly released at the same measured (1) inspiratory flow rate and (2) inspiratory volume. To maximize the efficiency of the delivery the narcotic formulation is released at (1) a measured inspiratory flow rate in the range of from about 0.10 to about 2.0 liters/second and (2) a measured inspiratory volume in the range of about 0.15 to about 0.8 liters. Abuse of narcotic formulations is avoided by providing a tamper-resistant device which includes a variety of security features including an electronic lock and key means and a pre-programmed microprocessor designed to avoid overdosing.

9 Claims, 7 Drawing Sheets

OTHER PUBLICATIONS

Chrusbasik, H. et al., "Absorption and bioavailability of nebulized morphine", 1988m Br. F. Anaesth. 61:228–230.

Gourlay, G.K., "Fentanyl Blood Concentration–Analgesic Response Relationship in the Treatment of Postoperative Pain", 1988, Anesth. Analg. 67:329–337.

Higgins, M.J. et al., 1991, "Inhaled nebulized fentanyl for postoperative analgesia", Anaesthia, 46:973–976.

Jaffe, A.B. et al., 1989, "Rats self–administer sufentanil in aerosol formm", Psychopharmacology, 99:289–293.

Lehman, K.A. et al., 1991, "Transdermal fentanyl for the treatment of pain after major urological operations", Eur. J. Clin. Pharmacol. 41:17–21.

Mather, L.E. "Pharmacokinetics and patient–controlled analgesia(*)", 1992, Acta Anaesthesiologica Belgica, 43:5–20.

Miller, R., "Anesthesia" (2nd ed), 1986, Churchill Livingstone, 1:762.

Newman, S.P. et al., "Deposition of pressurized aerosols in the human respiratory tract", 1981, Thorax, 36:52–55.

Newman, S.P. et al., "How should a pressurized β–adrenergic bronchodilator be inhaled?", 1981, Eur. J. Respir. Dis. 62:3–21.

Newman, S.P. et al., "Deposition of pressurized suspension aerosols inhaled through extension devices," 1981, Am. Rev. Respir. Dis. 124:317–320.

Newman, S.P. et al., "Deposition and Effects of Inhalation Aerosols," 1983, Dept. of Thoracic Medicine, Royal Free Hospital, London NW3 2QG.

Rapp, R.P. et al., "Patient–controlled analgesia:a review of effectiveness of therapy and an evaluation of currently available devices," 1989, DICP, The Annals of Pharmacotherapy 23:899–904.

Rosenberg, M., "Patient–Controlled Analgesia", 1992, J. Oral Maxillofac. Surg. 50:386–389.

Rowbotham, D.J., "A disposable device for patient–controlled analgesia with fentanyl", 1989, Anaesthesia, 44:922–924.

Ryder, E., "The history of patient–controlled analgesia", 1991, Journal of Intravenous Nursing, 14(6):372–381.

Shade, P., "Patient–controlled analgesia: can client education improve outcomes?", 1992, Journal of Advanced Nursing, 17:408–413.

Smythe, M., "Patient–controlled analgesia: a review", 1992, Pharmacotherapy, 12:132–143.

Stanley, T.H., "The history and development of the fentanyl series", 1992, Journal of Pain and Symptom Management, 7(Suppl.):S3–7.

Worsley, M.H. et al., "Inhaled fentanyl as a method of analgesia", Anaesthesia, 45:449–451.

LOCKOUT DEVICE FOR CONTROLLED RELEASE OF DRUG FROM PATIENT-ACTIVATED DISPENSER

CROSS-REFERENCES

This application is a continuation-in-part of earlier filed application Ser. No. 08/331,065, filed Oct. 28, 1994, now U.S. Pat. No. 5,507,277, which application is a continuation-in-part of application Ser. No. 08/011,289, filed Jan. 29, 1993, now abandoned which applications are incorporated herein by reference and to which applications is claimed priority under 35 U.S.C. §120.

FIELD OF THE INVENTION

This invention relates generally to controlling access to drugs contained in a drug delivery device. More specifically, this invention relates to a microprocessor controlled locking system that allows access to a narcotic drug only to an intended user possessing a uniquely coded machine readable access device specifically read by a locking system on a drug delivery device for intrapulmonary drug delivery.

BACKGROUND OF THE INVENTION

Controlled access to a drug or medication is of paramount importance in cases where the drug is a narcotic or is potentially toxic to an unintended user. A user for whom the drug is not intended, such as a child, may be harmed by such access. In the case of narcotics where the use of the drug is greatly restricted, unintended use is not only potentially dangerous but illegal.

However, the on-demand administration of drug (e.g., a narcotic, an analgesic, or a therapeutic, such as insulin) which allows the patient to control administration of his medication has proven to be an effective method of maintaining effective blood levels of the drug; or allows a rapid concentration increase of the drug for rapid physiological effect.

Narcotic therapy forms the mainstay of pain management. These drugs can be administered in many forms to patients with postsurgical and other forms of acute and chronic pain. Morphine, one of the oldest narcotics, is available for administration in tablet or in injectable form. Fentanyl, a synthetic narcotic, was first synthesized in 1960 by Paul Janssen and found to be 150 times more potent than morphine [Theodore Stanley, "The History and Development of the Fentanyl Series," *Journal of Pain and Symptom Management* (1992) 7:3 (suppl.), S3–S7]. Fentanyl and its relatives Sufentanil and Alfentanil are available for delivery by injection. In addition, fentanyl is available for administration by a transdermal delivery system in the form of a skin patch [Duragesic™ (fentanyl transdermal system) package insert, Janssen Pharmaceutica, Piscataway, N.J. 08855, January–June 1991].

A feature of the synthetic narcotic fentanyl is that is has a more rapid time to onset and a shorter duration of action than morphine. This makes fentanyl a useful drug for the management of acute pain. Currently, fentanyl is typically given by intravenous injection for acute pain management. Although fentanyl can be given by a transdermal patch, transdermal delivery of fentanyl is designed for long-term administration of the drug and does not lend itself to achieving a peak level rapidly for a short-term effect.

An alternative to delivery by injection for narcotics is delivery by inhalation. Morphine [J. Chrusbasik et al., "Absorption and Bioavailability of Nebulized Morphine," *Br. J. Anaesth.* (1988) 61, 228–30], fentanyl [M. H. Worsley et al., "Inhaled Fentanyl as a Method of Analgesia," *Anaesthesia* (1990) 45, 449–51], and sufentanil [A. B. Jaffe et al., "Rats Self-administer Sufentanil in Aerosol Form," *Psychopharmacology*, (1989) 99, 289–93] have been shown to be deliverable as aerosols into the lung. The pilot study described by Worsley suggested that "inhaled fentanyl is an effective, safe and convenient method of analgesia which merits further investigation."

Inhalation of a potent synthetic narcotic aerosol provides a mechanism for the non-invasive delivery of rapid-acting boluses of narcotic. The on-demand administration of boluses of narcotic coupled with a controlled baseline intravenous infusion of narcotic is termed "patient-controlled analgesia" (PCA) and has been found to be a very effective means of postoperative pain management.

On-demand analgesia was first introduced in 1968 by Schetzer who showed it to be an effective mechanism for treating postoperative patients [Maureen Smythe, "Patient-Controlled Analgesia: A Review," *Pharmacotherapy* (1992), 12:2, 132–43]. Prior to the availability of patient-controlled analgesia, the paradigm for postoperative pain management consisted of intermittent intramuscular injections of narcotic. The cycle of the patient feeling pain, calling the nurse who then must locate and bring the drug to the bedside for administration results in suboptimal postoperative pain management [Philip Shade, "Patient-controlled Analgesia: Can Client Education Improve Outcomes?," *Journal of Advanced Nursing* (1992) 17, 408–13]. Postoperative pain management by intermittent narcotic administration has been shown to be a largely ineffective method of pain management for many of the patients undergoing the more than 21 million surgical procedures in the United States each year [John Camp, "Patient-Controlled Analgesia," *AFP* (1991), 2145–2150]. Even if every patient reliably received a constant dose of narcotic postoperatively, studies of therapeutic narcotic pharmacokinetic data have shown that patient variability makes such an approach fundamentally unsound and potentially dangerous [L. E. Mather, "Pharmacokinetics and Patient-Controlled Analgesia," *Acta Anaesthesiologica Belgica* (1992) 43:1, 5–20].

The first commercial device for automatically providing intravenous patient-controlled analgesia was developed in Wales in the mid-1970s. This device, the Cardiff Palliator (Graesby Medical Limited, United Kingdom) is the predecessor of numerous currently available computer-controlled patient-controlled analgesia intravenous pumps [Elizabeth Ryder, "All about Patient-Controlled Analgesia," *Journal of Intravenous Nursing* (1991) 14, 372–81]. Studies using these computer controlled intravenous narcotic infusion pumps have shown that small doses of narcotics given on demand by the patient provided superior pain relief when compared with intermittent intramuscular administration of these drugs [Morton Rosenburg, "Patient-Controlled Analgesia," *J. Oral Maxillofac Surg* (1992) 50, 386–89].

These computer-controlled pumps typically allowed for the programming of four different parameters: 1) basal intravenous narcotic infusion rate; 2) the bolus of narcotic to be delivered on each patient demand; 3) the maximum hourly total dose of narcotic to be allowed; and 4) the lockout period between doses. Typical programming for postoperative pain management with intravenous fentanyl might be a basal infusion rate of 20 μg/hr, a bolus demand dose of 20 μg, a maximum hourly dose of 180 μg, and a lockout period between doses of 5 minutes. In a study of 30 patients treated for postoperative pain with intravenous fentanyl patient-controlled analgesia, the minimum effective concentration (MEC) of fentanyl in the blood required to achieve pain relief in the group of patients studies was found to range from 0.23 to 1.18 ng/ml. Clinically significant respiratory depression was not seen in this study consistent with published data indicating that a fentanyl concentration of 2 ng/ml in the blood is typically required to depress the respiratory rate [Geoffrey Gourlay et al., "Fentanyl Blood Concentration—Analgesic Response Relationship in the treatment of Postoperative Pain," *Anesth Analg* (1988) 67, 329–37].

The administration of narcotic for pain management is potentially dangerous because overdoses of narcotics will cause complications such as respiratory depression. The patient's respiratory rate is decreased by the administration of narcotics. This decrease in respiratory rate may not be associated with a change in respiratory tidal volume [Miller, *Anesthesia* (2nd ed), *Churchill Livingston, 1*, 762]. The four programmable parameters available on computer-controlled intravenous patient-controlled analgesia infusion pumps must be selected so as to minimize the likelihood of narcotic overdose. The preferred technique is to set the basal infusion rate at a relatively low rate and increase this rate based on how many times the patient presses the bolus demand button to self-administer supplemental drug.

As long as the patient himself or herself is the only one to push the demand button, respiratory depression is unlikely. However, there have been documented cases of the patient's family and friends pressing the narcotic demand button, for instance while the patient is sleeping [Robert Rapp et al., "Patient-controlled Analgesia: A Review of the Effectiveness of Therapy and an Evaluation of Currently Available Devices," *DICP, The Annals of Pharmacotherapy* (1989) 23, 899–9040].

It is a problem with patient-controlled analgesia that it must currently be performed using an intravenous infusion pump. This requires that an indwelling catheter be placed in the patient's vein and that the patient transport a relatively bulky system with himself at all times to receive a baseline infusion of intravenous narcotic and allow for intermittent on-demand self-bolusing of additional narcotic in order to match the patient's changing need for drug. A portable PCA device incorporating a wristwatch-like interface has been described [D. J. Rowbotham, "A Disposable Device for Patient-Controlled Analgesia with Fentanyl," *Anaesthesia* (1989) 44, 922–24]. This system incorporated some of the features of computer-controlled programmable PCA infusion pumps such as basal infusion rate and the amount of each bolus. However, this system, which involved the use of an intravenous catheter as seen in larger infusion pumps, incorporated no provision to record accurately the actual dose of Fentanyl administered to the patient over time.

Although fentanyl can be administered by transdermal patch, this method has been found to be suboptimal for postoperative main management [K. A. Lehmann et al., "Transdermal Fentanyl for the Treatment of Pain after Major Urological Operations, *Eur. J. Clin Pharmacol* (1991) 21:17–21]. Lehmann found that the low dose of narcotic delivered by transdermal fentanyl was inadequate to provide pain relief to many of his patients and that boosting the baseline infusion rate of the patch would put some patients at risk for having significant respiratory depression. In addition, he points out that if such a complication were to appear in conjunction with the delivery of narcotic by transdermal patch, the infusion could not be quickly stopped because the "cutaneous fentanyl depot" created by the transdermal patch would cause narcotic infusion to continue even after removal of the patch.

Delivery of fentanyl by aerosol used in conjunction with a non-invasively delivered long-acting preparation of narcotic such as slow-release oral morphine or a fentanyl transdermal patch provides a means for non-invasive administration of a basal rate of narcotic and rapid-acting boluses of narcotic to an ambulatory patient.

It is a problem with the aerosol delivery of fentanyl previously described that inefficient, bulky nebulizers must be used for the administration of the drug. In addition, these nebulizers work by administering from an open reservoir of the drug in aqueous solution allowing the vapor to be generally distributed and creating the potential for overdosing due to the lack of reproducible aerosol delivery. In addition, abuse through theft of the aqueous-phase fentanyl and subsequent unauthorized repackaging of this controlled substance in an aqueous injectable form are possible.

Because most surgery today is being done on ambulatory patients and because these patients are often rapidly discharged from the hospital and because patient-controlled analgesia has been identified as the preferred method of postoperative pain management, it is desirable to have a safe, effective, and access-controlled method for non-invasive, ambulatory patient-controlled analgesia.

SUMMARY OF THE INVENTION

The present invention relates to a package containing medicine, the package being constructed so that it is difficult to open the package without contacting a sensor on the package to a mating receptacle (such as a serialized semiconductor) possessed by the patient for whom the medicine is intended. The mating receptacle bears a machine readable code indicating the identity of the patient that is matched to the package containing the medicine. Contacting the package sensor to the serialized semiconductor provides a keying feature to allow the patient access to the medicine.

A particular and preferred means for permitting the package to be activated by the patient, a Touch Serial Number (TSN, manufactured by Dallas Semiconductor) as termed herein, includes a semiconductor encoded with a device family code, a unique 48 bit serial number (providing $2.8\times10^{14}$ possible combinations), and a cyclic redundancy check (hereinafter CRC) byte, all housed in a metallic container. The front surface of the container serves as one electrical contact, while the back and side surfaces of the container serve as the other electrical contact providing a 2-wire serial interface that allows the mating receptacle to be reset; a command word to be written into the TSN; and data to be read from the TSN.

A TSN is preferably attached to a means (such as a bracelet or badge) that allows the patient to wear the TSN. The package containing the medicine will include a microcomputer programmed with the family code, serial number and CRC byte of the matching TSN and will include a TSN-compatible serial port for contact with the TSN.

Programming of the microcomputer is accomplished by setting the microcomputer to "learn" mode with a command sent by computer via the package's serial port. The TSN is then contacted to the package's serial port, allowing the microcomputer within the package to read the TSN's data and store the data in the microcomputer's internal non-volatile memory.

In a preferred method of using the device, the user will have approximately three seconds after turning on the package to contact his or her TSN to the serial port. The package will then send a reset signal from the TSN port. If no TSN is attached, no acknowledgement of the reset signal will occur; the package will display an error message and halt activation of the drug delivery mechanism. If a TSN is attached to the package, the reset signal will be acknowledged. The package microcomputer will respond by first sending a "read" command byte to the TSN. The microcomputer then reads the next 64 bits from the TSN's ROM. After each byte is read, it is compared to the corresponding serial number byte pre-programmed into the drug delivery device. When a comparison fails, such as when an invalid TSN or no TSN is contacted to the serial port, the microcomputer is preferably programmed to display an error message and halt activation of the device. Preferably, the comparison and activation or deactivation operation occurs in approximately 15 ms or less. In a preferred embodiment, 8 bytes are read from the TSN and compared to the serial number pre-programmed into the drug delivery device. If the codes match, the drug delivery device will allow operation, giving the user time to administer a dose of the drug before the microcomputer deactivates the power source to the device. Preferably, the TSN is removed from the device after the serial number has been read by the device's microcomputer.

Another preferred embodiment of the invention is to require contact, reading, and comparison steps of the microcomputer to be performed during the mechanical drug delivery step. In this embodiment, the drug delivery device (such as a syringe, aerosol inhalant, or like) can be turned on but the activation of the delivery mechanism will not occur unless the contact, reading, and comparison steps are successfully performed and the serial numbers of the TSN and the drug delivery device match.

It is also an object of the invention to disclose a method of pain control provided by the intrapulmonary delivery of a pharmaceutically active pain relief formulation. After electronically unlocking the drug delivery device formulation is automatically released from a hand-held, self-contained, portable device. The device is comprised of the above-described locking components, a means for automatically releasing a separately measured amount of drug into the inspiratory flow path of a patient in response to information obtained from determining, in real time, both the inspiratory flow rate and inspiratory volume of a patient. Reproducible dosing is obtained by providing for automatic release in response to a measured inspiratory rate and inspiratory volume. The method involves measuring for, calculating and/or determining a firing point or drug release decision based on the instantaneously (or real time) calculated, measured and/or determined inspiratory flow rate and inspiratory volume points. To obtain repeatability in dosing the narcotic formulation is repeatedly released at the same measured (1) inspiratory flow rate and (2) inspiratory volume. To maximize the efficiency of the delivery the narcotic formulation is released at (1) a measured inspiratory flow rate in the range of from about 0.10 to about 2.0 liters/second and (2) a measured inspiratory volume in the range of about 0.15 to about 0.8 liters. The device may include other security features such as a pre-programmed microprocessor designed to avoid overdosing and may include the narcotic in a low boiling point solvent so that opening the container results in essentially immediate loss of the entire contents of the container as the solvent vaporizes.

It is an object of this invention to describe a method of aerosolized delivery of potent narcotic in a safe and effective manner.

It is another object of the invention to describe a method of restricting access to a potent narcotic in a drug delivery device, such as an aerosol delivery device and a lock and key mechanism (such as an electronic key) that allows the intended user access to the drug and prevents access by unintended users. In a preferred embodiment the user touches his uniquely coded, machine readable key (such as a TSN) to a lock portion (such as a TSN interface) capable of reading the key and discerning a match or mismatch of the unique code of the key and the locking portion. A code match results in the release of a lock on activation of the drug delivery device allowing the user to receive a dose of the drug.

Another object of the invention is to provide controlled access to a narcotic drug in an aerosol drug delivery device by providing an electronic key for access control whereby the locking portion of the electronic key is affixed to the aerosol container and the key portion of the electronic key is affixed to a substrate that is carried or worn by the user (e.g., a bracelet, a badge, a card, or the like).

An advantage of the invention is that the drug contained in the controlled access drug delivery device is accessible only to an intended user.

Another advantage of the invention in one embodiment the drug is dissolved in a solvent that vaporizes at normal atmospheric pressure. Bypassing the electronic key access mechanism to access the drug requires breaking open the pressurized drug-containing canister. When the canister is opened to atmospheric pressure, the entire contents is immediately dispersed making the drug unavailable to the unintended user.

Another advantage of the invention is that a controlled-access drug delivery device prevents access to unintended users and will therefore offer less liability risk to the manufacturer and the supplier of the device.

Another advantage of the invention is that the controlled access drug delivery device prevents access to the drug by children making it possible for the user to treat himself in his home.

Yet another advantage of the invention is that the electronic key provides a unique coding of each drug delivery device and its associated key such that one or more devices can be programmed with a unique code that is also encoded on the key portion (such as a TSN) of the electronic key device.

An advantage of the present invention is that it can be used for ambulatory patients with a significantly reduced risk of narcotic abuse.

Another object is to provide a method of managing the pain of ambulatory patients wherein aerosolized narcotic formulation is repeatedly delivered to the patient at the same measured inspiratory volume (in the range of 0.15 to 0.8 liters and the same measured inspiratory flow rate (in the range of 0.1 to 2.0 liters per sec) after electronically unlocking the delivery device.

Another feature of this invention is that formulations of narcotics such as fentanyl and a highly volatile propellant provide for a fundamentally tamper-resistant package making it difficult for the contained fentanyl to be illicitly repackaged in an injectable form.

It is another object of the invention to provide a metered-dose inhaler canister comprising a formulation of narcotic such as fentanyl packaged in a manner such that it can only be used in conjunction with a particular electronically locked apparatus described.

Another advantage is that the device can be programmed to provide a minimum required time interval between doses.

Another advantage of the invention is that the device can be programmed so as to control the maximum amount of narcotic delivered within a period of time.

Still another advantage is that dosing of narcotics can be controlled so that aerosol delivery is possible and patients can obtain quick pain relief using such.

Yet another advantage is to provide a device which can be electronically locked and simultaneously programmed to control the maximum amount of narcotic drug delivered within a given period of time and provide for a minimum required time interval between the delivery of doses.

A feature of the invention is that it can monitor the amount of aerosolized narcotic delivered to a patient (e.g. mg of formulation) and record amounts and times of delivery for review by a treating physician.

Another advantage of the invention is that the apparatus can monitor respiratory rate to ensure that respiratory depression has not supervened prior to further administration of narcotic.

Another object of this invention is to provide an apparatus which can be electronically locked and can analyze the breathing pattern of the patient not only to determine the respiratory rate prior to delivery but also to determine the inspiratory flow profile characteristics so as to determine the optimal point in the inspiratory cycle for delivery of aerosolized potent narcotic.

Yet another object of this invention is to further provide aerosolized naloxone which may be administered to counteract the effects of administered potent narcotic in the event of the development of complications such as respiratory depression due to overdose of the narcotic.

Another advantage is that the method described provides for electronically coded access and reproducible delivery of narcotics such as fentanyl wherein the reproducibility is a critical part of safety causing each dose of narcotic to have the same clinical effect.

Another object is to provide an electronic lock-and-key system which allows only the intended authorized patient to inhale aerosolized narcotic from the described apparatus.

These and other objects, advantages and features of the present invention will become apparent to those skilled in the art upon reading this disclosure in combination with drawings wherein like numerals refer to like components throughout.

BRIEF DESCRIPTION OF THE DRAWINGS

FIG. 1 is a cross-sectional view of a drug delivery device;

FIG. 2 is a cross-sectional view of a more preferred embodiment of a drug delivery device;

FIG. 3 is a perspective view showing a pressurized canister with the canister cover components disconnected;

FIG. 4 is a perspective view of another embodiment of the cover components connected and the canister held therein;

FIG. 5 is a graph showing data points plotted in four general areas with the points plotted relative to inspiratory flow rate (on the abscissa) and inspiratory volume (on the ordinate) in two dimensions;

FIG. 6 is a graph showing the four general areas plotted per FIG. 1 now plotted with a third dimension to show the percentage of drug reaching the lungs based on a constant amount of drug released;

FIG. 7 is a three dimensional graph showing the therapeutic values for inspiratory flow rate and inspiratory volume which provide better drug delivery efficiency;

FIG. 8 shows a preferred range of the valves shown in FIG. 7;

FIG. 9 shown a particularly preferred range for the valves of FIG. 7;

FIG. 10 is a schematic diagram of an aqueous system drug delivery device; and FIG. 11 is a schematic diagram of an unauthorized user lockout flowchart showing decisions made by the device in allowing access to the drug delivery device.

DETAILED DESCRIPTION OF THE PREFERRED EMBODIMENTS

Before the present method of pain management with electronically controlled access and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an electronic access device" includes a plurality of such devices, and reference to "the method of preventing access" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The term "electronic key" refers to a means for providing a unique identifying code to a component which prevents access to a device. In general, an electronic key locking unit on the drug delivery device is activated or unlocked by an electronic key possessed by the intended user. Use of the drug delivery device is prevented without the use of the electronic key.

The term "intended user" refers to a user to whom the drug contained in the drug delivery device of the invention is prescribed such by a prescribing physician. The intended user is the only person who is intended to possess the correct electronic key which may be a programmed TSN that matches the code of the TSN interface on the user's drug delivery device.

The term "unintended user" refers to individuals who do not possess a TSN which matches the code of the TSN interface on the user's drug delivery device.

The term "velocity of the drug" shall mean the average speed of particles moving from a drug release point such as a valve to a patient's mouth.

The term "dosing event" shall be interpreted to mean the administration of analgesic drug to a patient in need thereof by the intrapulmonary route of administration which event may encompass electronically unlocking a device followed by one or more releases of analgesic drug formulation from an analgesic drug dispensing device over a period of time of 15 minutes or less, preferably 10 minutes or less, and more preferably 5 minutes or less, during which period multiple inhalations are made by the patient and multiple doses of analgesic drug are released and inhaled. A dosing event shall involve the administration of analgesic drug to the patient in an amount of about 1 µg to about 100 mg in a single dosing event which may involve the release of from about 10 µg to about 1000 mg of analgesic drug from the device.

The term "measuring" describes an event whereby both the inspiratory flow rate and inspiratory volume of the patient is measured, calculated and/or determined in order to determine an optimal point in the inspiratory cycle at which to release aerosolized narcotic formulation. It is also preferable to continue measuring inspiratory flow during and after any drug delivery and to record inspiratory flow rate and volume before, during and after the release of drug. Such reading makes it possible to determine if narcotic formulation was properly delivered to the patient. A microprocessor or other device can calculate volume based on a measured flow rate. When either flow rate or volume becomes known in any manner it can be said to have been determined.

The term "monitoring" event shall mean measuring lung functions such as inspiratory flow, inspiratory flow rate, and/or inspiratory volume so that a patient's lung function as defined herein, can be evaluated before and/or after drug delivery thereby making it possible to evaluate the effect of narcotic delivery on the patient's lung function.

The term "inspiratory flow rate" shall mean a value of air flow measured, calculated and/or determined based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure ±5% and temperature in the range of about 10° C. to about 40° C.

The term "inspiratory volume" shall mean a measured, calculated and/or determined volume of air passing a given point into the lungs of a patient assuming atmospheric pressure ±5% and a temperature in the range of 10° C. to 40° C.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. The point within the inspiratory cycle where drug is released may be based on a point within the inspiratory cycle likely to result in the maximum delivery of drug and based and/or on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "analgesic drug" shall be interpreted to mean a drug for treating symptoms of pain. Analgesic drugs may include one of: narcotics, nonsteroidal anti-inflammatory drugs and mixed agonist-antagonistic drugs such as butorphanol. Examples of useful narcotics drugs are described and disclosed within the Physicians Desk Reference and the Drug Evaluations Annual 1993, published by the American Medical Association, both of which are incorporated herein by reference. The invention encompasses the free acids, free bases, salts, hydrates in various formulations of analgesic drugs useful for pain control.

The term "therapeutic index" refers to the therapeutic index of a drug defined as $LD_{50}/ED_{50}$. The $LD_{50}$ (lethal dose, 50%) is defined as the dose of a drug which kills 50% of the tested animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active drug by itself or with a pharmaceutically acceptable carrier in flowable form which is preferably a liquid. Such formulations are preferably solutions, e.g. aqueous solutions, ethanolic solutions, aqueous/ethanolic solutions, saline solutions and colloidal suspensions. Formulations can be solutions or suspensions of drug in a low boiling point propellant.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Quantitative determination of pulmonary function may be important when delivering analgesic drugs in that respiration can be hindered or stopped by the overdose of such drugs. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

In addition to the respiratory parameters measured by the device, the device is further equipped to be activated (unlocked) and deactivated (locked) by an electronic key device (such as the Touch Serial Number device supplied by Dallas Semiconductor). The device is electronically connected by means well known to those of skill in the art of electronics to the activation and/or actuation of the drug delivery device so as to control access to delivery of a drug contained in the device.

The term "CRC" is an abbreviation for cyclic redundancy check. A cyclic redundancy check or CRC is used in the TSN device and provides a technique which generates a byte-wide value based on the devices family code and serial number data—this number could then be used to verify the integrity of the data downloaded from the drug delivery device from the TSN device. To perform the integrity check, the drug delivery device would apply the CRC generation algorithm to data received from the TSN. After all the data has been transferred, the drug delivery device would compare the CRC value it calculated from the data stream against the CRC byte transmitted by the TSN. If the values match, the drug delivery device would assume no errors occurred during the data transmission. Otherwise, the drug delivery device would request that the TSN data be retransmitted. Unless the correct data is transmitted to the microprocessor of the drug delivery device the drug device cannot be activated and drug cannot be released from the device.

General Methodology

The device and methodology make it possible to electronically control access to a drug (such as a toxic or narcotic drug) prescribed to a specific patient such that only the patient has access to the drug in the intended dosages. The preferred means of controlling access is an electronic key device with a uniquely coded key means (such as a TSN) and a lock means (such as a TSN interface) capable of reading the unique code and matching the code to a unique code in the internal memory of the lock means. If the codes match, the drug delivery device receives an acknowledgement signal, the drug delivery device is activated and the user is able to access the drug. If the codes do not match, or if no key means is available, the drug delivery device receives no acknowledgement signal and the drug delivery device is not activated and will not dispense drug.

A non-invasive means of pain management is provided in a manner which makes it possible to restrict access and maintain tight control over the amount of drug administered to a patient suffering with pain and to quickly and efficiently provide for pain relief. An essential feature of the invention is controlled access of intrapulmonary delivery of analgesic drug to the patient combined with drug delivery in a controlled and repeatable manner. The device of the invention provides a number of features which make it possible to control access and achieve the controlled and repeatable dosing procedure required for pain management. Specifically, the device is electronically locked and drug is not directly released by the patient in the sense that no button is pushed nor valve released by the patient applying physical pressure. On the contrary, the device of the invention provides that the valve releasing analgesic drug is unlocked with an electronic key after which the valve is opened automatically upon receipt of a signal from a microprocessor programmed to send a signal when data is received from a monitoring device such as an airflow rate monitoring device. A patient using the device withdraws air from a mouthpiece and the inspiratory rate, and calculated inspiratory volume of the patient is measured one or more times in a monitoring event which determines an optimal point in an inhalation cycle for the release of a dose of analgesic drug. Inspiratory flow is measured and recorded in one or more monitoring events for a given patient in order to develop an inspiratory flow profile for the patient. The recorded information is analyzed by the microprocessor in order to deduce a preferred point within the patient's inspiratory cycle for the release of analgesic drug with the preferred point being calculated based on the most likely point to result in a reproducible delivery event.

It is pointed out that the device of the present invention can be used to, and actually does, improve the efficiency of drug delivery. However, this is not the critical feature. The critical feature is controlled access along with reproducibility of the release of a tightly controlled amount of drug at a particular point in the respiratory cycle so as to assure the delivery of a controlled and repeatable amount of drug to the lungs of each individual patient.

The combination of controlled access and automatic control of the valve release, combined with frequent monitoring events in order to calculate the optimal flow rate and time for the release of analgesic drug, combine to provide a repeatable means of delivering analgesic drug to a patient. Because the valve is released automatically and not manually, it can be predictably and repeatedly opened for the same amount of time each time or for the preprogrammed measured amount of time which is desired at that particular dosing event. Because dosing events are preferably preceded by monitoring events, the amount of analgesic drug released and/or the point in the inspiratory cycle of the release can be readjusted based on the particular condition of the patient. For example, if the patient is suffering from a condition which allows for a certain degree of pulmonary insufficiency, such will be taken into account in the monitoring event by the microprocessor which will readjust the amount and/or point of release of the analgesic drug in a manner calculated to provide for the administration of the same amount of analgesic drug to the patient at each dosing event.

Figure 5:
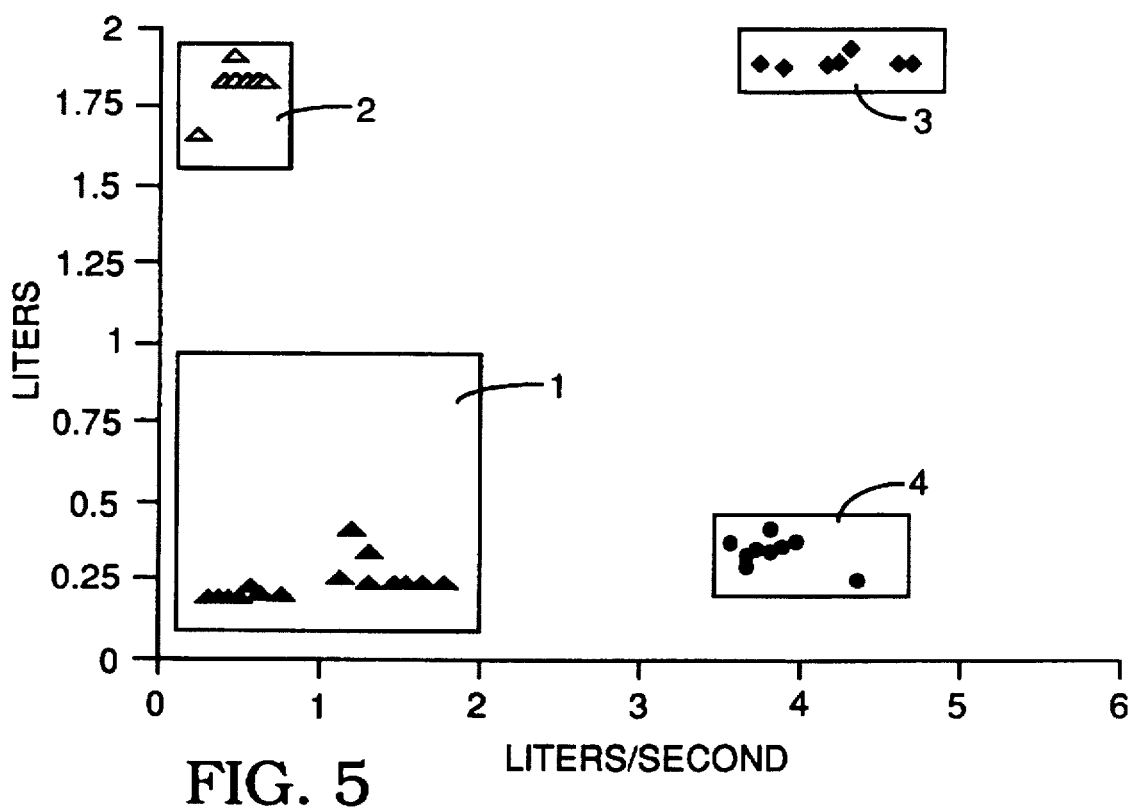

FIG. 5 is a two-dimensional graph wherein the inspiratory flow rate is plotted against the inspiratory volume. The patient's inspiratory flow rate and inspiratory volume may be simultaneously and separately measured, calculated and/or determined. The measurement is taken and the information obtained from the measurement provided to a microprocessor which microprocessor is programmed to release drug (1) at the same point relative to inspiratory flow and inspiratory volume at each release of drug and (2) to select that point within prescribed parameters of inspiratory flow rates and inspiratory volumes. In the particular results plotted in FIG. 5 the microprocessor was programmed to release drug in four general areas with respect to the inspiratory flow rate and inspiratory volume parameters. This resulted in data points being plotted in four general areas on the two-dimensional graph of FIG. 5. The four areas are labeled 1, 2, 3 and 4. In area 1 (showing solid triangles), the drug was released when the patient's inspiratory flow rate was "slow to medium" (0.10 to 2.0 liters per sec) with an "early" inspiratory volume of 0.15 to 0.8 liters. In area 2 (showing open triangles), the drug was released at a "slow" inspiratory rate/0.10 to 1.0 liters/sec) and a "late" volume (1.6 to 2.8 liters). In area 3 (showing solid diamonds), the drug was released at a "fast" inspiratory flow rate (3.5 to 4.5 liters/sec) and a "late" volume. In area 4 (showing solid circles), the drug was released at a "fast inspiratory flow rate and an "early" inspiratory volume.

The results shown in FIG. 5 were obtained while administering a radioactively labeled drug to a human. After the administration of the drug it was possible to determine not only the amount of drug, but the pattern of drug deposited within the lungs of the patient. Using this information two conclusions were reached. Firstly, it was determined that it is important to simultaneously and separately determined (in real time) both inspiratory flow rate and inspiratory volume when providing for intrapulmonary drug delivery. Changes in either parameter can greatly effect the amount of drug deposited. Thus, when treating a patient the drug should be released at approximately (±10%, preferably ±5% and most preferable as close as possible to the first release point) the same inspiratory flow rate and inspiratory volume each time—going back to the same point each time for the same patient ensures repeatable dosing. In practice the tighter the point is defined the greater the repeatability of dosing. However, if the point is defined to precisely it can be difficult for the patient to obtain that rate/volume point again. Thus, some degree of tolerance is generally applied. Secondly, it was found that within particular ranges with respect to inspiratory flow rate and inspiratory volume it was possible to obtain a consistently high percentage amount of drug deposited in the lung. Such results are shown graphically within the three dimensional graph as shown in FIG. 6.

Figure 6:
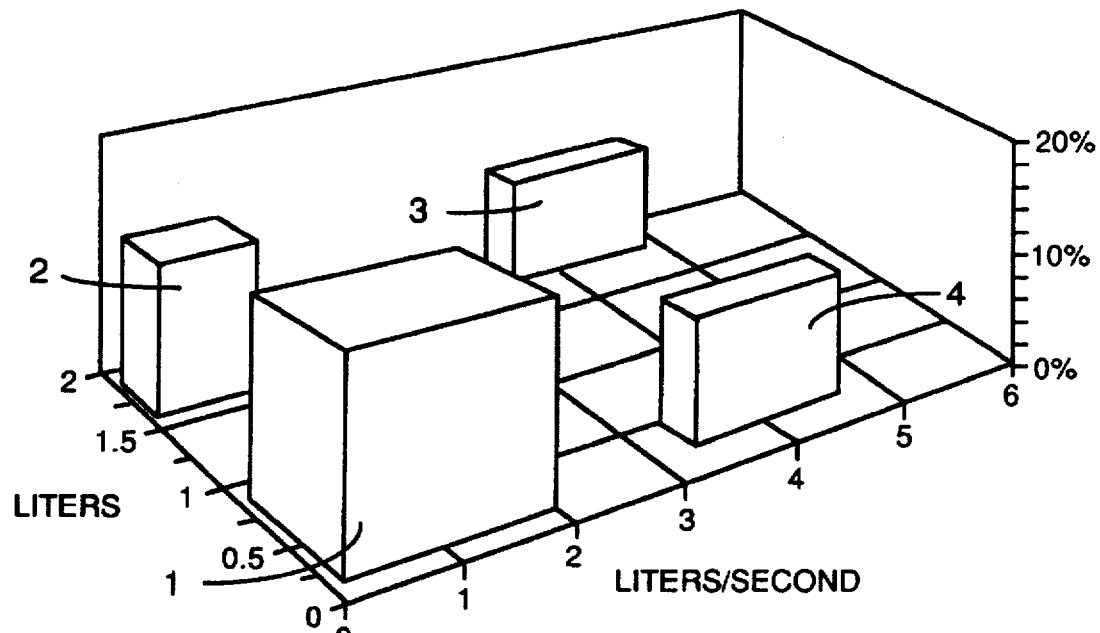

The third dimension as shown in FIG. 6 (the height of the four columns) indicates the percentage amount of drug deposited based on the total amount of drug released to the patient. The area labeled 1 clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within an inspiratory flow rate range of 0.10 to 2.0 liters per second and at an inspiratory volume in the range of about 0.15 to about 0.80 liters. This range is shown by the rectangularly shaped column of FIG. 7.

In that intrapulmonary drug delivery systems often provide for erratic dosing it is important to provide a method which allows for consistent, repeatable dosing. This is obtained by simultaneously and separately measuring both inspiratory flow rate and inspiratory volume a defining point by its abscissa and ordinate. If both measurements are separately taken the drug can be released anywhere along the abscissa and ordinate scales shown in FIG. 5. Once a point is selected (such as by randomly selecting a point in box 1 of the graph of FIG. 5) that selected point (with the same coordinates) is used again and again by a given patient to obtain repeatable dosing. If only one parameter is measured (abscissa or ordinate) and drug is released based on that parameter the drug release point is defined by a line on the graph of FIG. 5. When drug is released again the release can be at any point on that line. For example, the inspiratory flow rate (measured horizontally on the abscissa) might be defined by a point. However, the inspiratory volume (which was not measured) would be defined only by a vertical line. Thus, subsequent releases would be at different volumes along that vertical line and the dosing would not be consistent. By measuring both inspiratory flow rate on the abscissa and inspiratory volume on the ordinant the coordinants will mark a point for drug release. That point can be found again and again to obtain repeatability in dosing. The same point should be selected each time as closely as possible and within a margin of errors of ±10% with respect to each criteria. The margin for error can be increased and still maintain acceptable levels of repeatable dosing—but the error should keep the drug release point inside the box 1 of FIG. 5.

Figure 7:
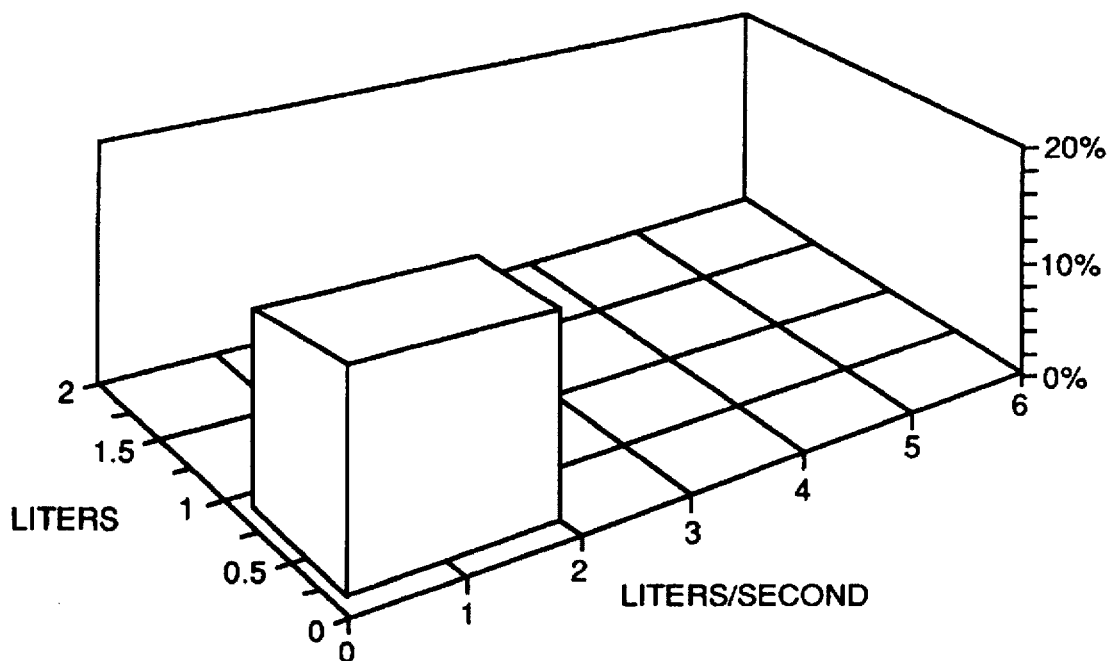
Figure 8:
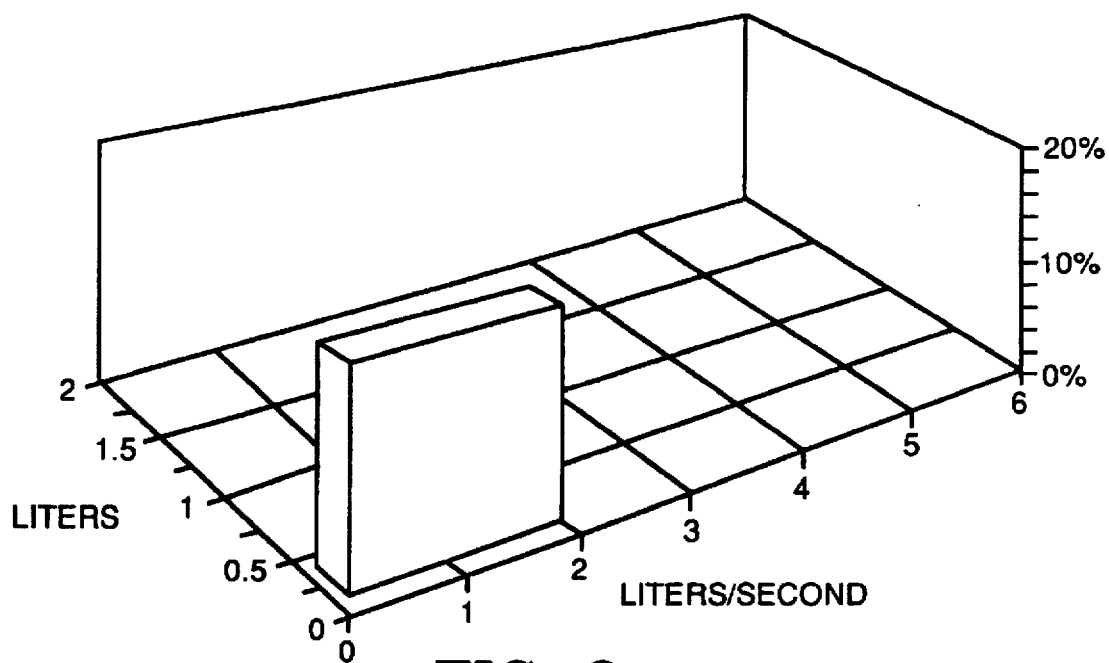
Figure 9:
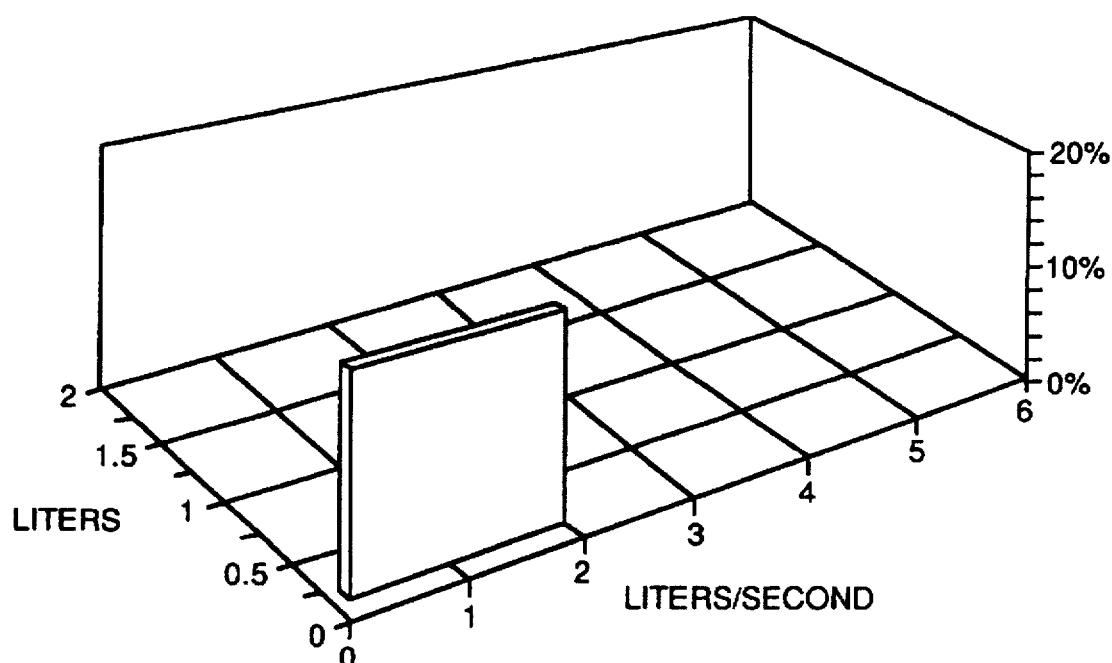

By examining delivery of drug associated with the data points plotted in FIG. 5, it is possible to determine a preferred and particularly preferred and most preferred range as per FIGS. 7, 8 and 9. The preferred range of FIG. 7 shows drug released at a volume of 0.15 to 0.8 liters and rate of 0.10 to 2.0 liters/second. The particularly preferred range plotted in FIG. 8 indicates that the inspiratory flow should be within the range of 0.2 to about 1.8 liters per second with an inspiratory volume in the range of 0.15 to about 0.4 liters. The most preferred range (FIG. 9) is from about 0.15 to about 1.8 liters per second for the inspiratory flow rate and about 0.15 to about 0.25 liters for the inspiratory volume. Thus, the essence of the invention is (1) repeatedly delivering aerosolized analgesic formulation to a patient at the same simultaneously and separately measured inspiratory flow rate and inspiratory volume and (2) releasing drug to the patient within specified therapeutically effective ranges as shown within FIGS. 7, 8 and 9. The invention involves releasing drug (after measuring) inside the ranges as per FIGS. 7, 8 or 9. Thus, the release could begin inside or outside the range. Preferable the drug release begins inside the range and more preferable begins and ends inside the ranges of FIGS. 7, 8 or 9.

The methodology of the invention may be carried out using a portable, hand-held, battery-powered device. As per U.S. patent application Ser. No. 08/002,507 filed Jan. 29, 1993 incorporated herein by reference. In accordance with another system the methodology of the invention could be carried out using the device, dosage units and system disclosed in U.S. patent application Ser. No. 08/247,012 filed May 20, 1994. In accordance with the system the analgesic drug (which is preferably a narcotic) is included in an aqueous formulation which is aerosolized by moving the formulation through a porous membrane. Alternatively, the methodology of the invention could be carried out using a mechanical (non-electronic) device. Those skilled in the art recognized that various components can be mechanically set to actuate at a given inspiratory flow rate (e.g. a spring biased valve) and at a given volume (e.g. a spinable flywheel which rotates a given amount per a given volume). The components of such devices could be set to allow drug release inside the parameters of FIGS. 3, 4 or 5.

The drug which is released to the patient may be in a variety of different forms. For example, the drug may be an aqueous solution of drug, i.e., drug dissolved in water and formed into small particles to create an aerosol which is delivered to the patient. Alternatively, the drug may be in a solution wherein a low-boiling point propellant is used as a solvent. In yet, another embodiment the drug may be in the form of a dry powder which is intermixed with an airflow in order to provide for particleized delivery of drug to the patient. Regardless of the type of drug or the form of the drug formulation, it is preferable to create drug particles having a size in the range of about 0.5 to 5 microns. By creating drug particles which have a relatively narrow range of size, it is possible to further increase the efficiency of the drug delivery system and improve the repeatability of the dosing. Thus, it is preferable that the particles not only have a size in the range of 0.5 to 5 microns but that the mean particle size be within a narrow range so that 80% or more of the particles being delivered to a patient have a particle diameter which is within ±50% of the average particle size, preferably ±20% and more preferably ±5% of the average particle size.

The velocity at which the aerosolized drug is released to the patient is also important in terms of obtaining a high degree of repeatability in dosing and providing for a high percentage of drug being delivered to the patient's lungs. Most preferably, the drug is released from a container in a direction which is normal to the patient's airflow. Accordingly, the drug may be released directly upward so that its flow is at a 90° angle with respect to the patient's inspiratory flow which is directly horizontal. After being released, the drug velocity decreases and the drug particles remain suspended for a sufficient period of time to allow the patient's inspiration to draw the drug into the patient's lungs. The velocity of drug released in the direction from the drug release point to the patient may match the patient's inspiratory flow rate but is preferably slower that the patient's inspiratory flow rate and is most preferably about zero. The velocity may be slightly negative, i.e., in a direction away from the patient. The velocity may range from −2.0 liters/sec to 2.0 liters/sec and is preferably zero. It is not desirable to project the drug toward the patient at a rate above the speed of the patient's breath as such may result in drug being deposited on the back of the patient's throat. Thus, the drug release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less. In general, the shorter the distance required to slow the particles to zero velocity the better.

An aerosol may be created by forcing drug through pores of a membrane which pores have a size in the range of about 0.25 to 2.5 microns. When the pores have this size the particles which escape through the pores to create the aerosol will have a diameter in the range of 0.5 to 5 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a diameter in the range of about 0.5 to 5 microns.

The drug formulation may be a low viscosity liquid formulation which is preferably a formulation which can be aerosolized easily and includes respiratory drug formulations currently used in nebulizers. The viscosity of the drug by itself or in combination with a carrier must be sufficiently low so that the formulation can be forced out of openings to form an aerosol, e.g., using 20 to 200 psi to form an aerosol preferably having a particle size in the range of about 0.5 to 5 microns.

Drug may be stored in and/or released from a container of any desired size. In most cases the size of the container is not directly related to the amount of drug being delivered in that most formulations include relatively large amounts of excipient material e.g. water or a saline solution. Accordingly, a given size container could include a wide range of different doses by varying drug concentration.

The amount of analgesic drug delivered to the patient will vary greatly depending on the particular drug being delivered. In accordance with the present invention it is possible to deliver a wide range of analgesic drugs. For example, drugs included within the container could be drugs which have a systemic effect such as narcotic drugs, for example morphine, fentanyl and sufentanil. Other useful drugs include those in a class known as NSAID's or non-steroidal anti-inflammatory drugs—particularly ketorolac and including acetaminophen and ibuprofen.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurred following the initial release of drug. The information recorded could then be read by a separate device, interpreted by the care-giver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the drug using the proper techniques and still not obtained the correct results a different drug or dosing methodology might be recommended.

The method of managing a patient's pain may be carried out using a hand-held, portable device comprised of (a) a device for holding a disposable package comprised of at least one but preferably a number of drug containers, (b) a propellant or a mechanical mechanism for moving the contents of a container through a porous membrane to create an aerosol, and (c) an electronic access control device which prevents release of drug unless activated by an electronic key. The device also preferably includes (d) a monitor for analyzing the inspiratory flow, rate and volume of a patient, and (e) a switch for automatically releasing or firing the mechanical means after the inspiratory flow and/or volume reaches a threshold level. The device may also include a transport mechanism to move the package from one container to the next. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means (and/or a vibration device below the resonance cavity). When the actuation means is signaled, it causes the mechanical means (by pressure or vibration) to move drug from a container on the package into the inspiratory flow path of the device and ultimately into the patient's lungs. After being released, the drug and carrier will pass through a porous membrane which is vibrated to aerosolize the formulation and thereafter the lungs of the patient. Containers and systems of the type described above are disclosed and described in U.S. patent application Ser. No. 08/247,012 filed May 20, 1994 which is incorporated herein by reference to disclose and describe such containers and systems.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of (1) reproducibly delivering the same amount of drug to the patient with each release of drug by releasing drug at the same point each time and maximizing the amount of drug delivered as a percentage of the total amount of drug released by releasing with the parameters described herein.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

The details of a drug delivery device which includes a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and it is specifically incorporated in order to describe and disclose the microprocessor and program technology used therewith. (See also PCT application 92-01815 also incorporated by reference.)

The use of such a microprocessor with a drug delivery device is disclosed in our earlier filed U.S. patent application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these three embodiments, changing the programming of the memory device readable by a microprocessor will radically change the behavior of the device by causing the microprocessor to be programmed in a different manner. This is done to accommodate different drugs for different types of treatment.

In a preferred embodiment of the methodology of the invention several different criteria are considered. (1) The inspiratory flow rate and inspiratory volume are simultaneously and separately measured to insure repeatability. (2) The drug is released inside the parameters of FIGS. 7, 8 or 9 with FIG. 9 parameters being most preferred. (3) The particle size of the released drug is in the range of 0.5 to 5 microns and 80% or more and the particles have the same size as the average particle size ±10% in size. (4) The drug particles are released at a velocity which is obtained at a flow rate in the range of greater than −2.0 liters/sec. and less than 2.0 liters/sec. As indicated early the actual velocity can vary based on a number of factors. The release velocity should be determined so that the particles are at or are slowed to zero velocity after traveling about 0.5 to 2 cm from the release point. The speed being measured from the drug release point in a direction toward the back of the throat of the patient.

After dosing a patient with a systemic analgesic drug it is desirable to take blood samples and make adjustments as needed to obtain the desired drug to blood ratio. In accordance with all methods the patient does not push a button to release drug. The drug is released automatically by signals from the microprocessor using measurements obtained. In another embodiment of the invention whereby the blood level of the drug is monitored and recorded in a machine readable format, the drug delivery device (such as an aerosol delivery device) can be programmed to restrict access to the drug by a user whose blood level of the drug (or rate of respiration) is in an unacceptable range. For example, a probe that monitors blood drug level in a machine readable format (or respiration rate monitor) can be coupled to a microprocessor electronically connected to the activation mechanism of the drug delivery device. Upon reading the data from the probe the electronic lock means may be signalled to provide access or not depending on whether the probe reading falls within a preprogrammed acceptable range of values.

The amount of analgesic drug delivered to the patient will vary greatly depending on the particular drug being delivered. In accordance with the present invention it is possible to deliver a wide range of different analgesic and narcotic drugs with a preferred drug being sufentanil which is generally administered to a patient in an amount in the range of about 2.5 µg–100 µg. It is pointed out that sufentanil is approximately ten times more potent than fentanyl (another preferred drug) so that fentanyl is generally delivered to a patient in an amount of about 25 µg–1000 µg. These doses are based on the assumption that when interpulmonary delivery methodology is used the efficiency of the delivery is approximately 10% and adjustments in the amount released must be made in order to take into account the efficiency of the device. The differential between the amount of analgesic drug actually released from the device and the amount of analgesic drug actually delivered to the patient varies due to a number of factors. In general, devices used with the present invention can have an efficiency as low as 10% and as high as 50% meaning that as little as 10% of the released analgesic drug may actually reach the circulatory system of the patient and as much as 50% might be delivered. The efficiency of the delivery will vary somewhat from patient to patient and must be taken into account when programming the device for the release of analgesic drug. In general, a conventional metered dose inhaling device is about 10% efficient.

When administering analgesic drug, the entire dosing event can involve the administration of anywhere from 1 µg to 100 mg, but more preferably involves the administration of approximately 10 µg to 10 mg. The large variation in the amounts which might be delivered are due to the fact that different drugs have greatly different potencies and may be delivered from devices which vary greatly in terms of the efficiency of drug delivered. The entire dosing event may involve several inhalations by the patient with each of the inhalations being provided with multiple bursts of analgesic drug from the device.

In addition to drug potency and delivery efficiency, analgesic drug sensitivity must be taken into consideration. The present invention makes it possible to vary dosing over time if analgesic sensitivity changes and/or if user compliance and/or lung efficiency changes over time.

Dynamic Particle Size Adjustment

The size of aerosolized particles released from a drug delivery device can change based on the surrounding atmosphere. For example, the particles can decrease in size due to evaporation of water from the particles or can increase in size due to the presence of a high concentration of water vapor within the air, i.e., high humidity. In order to compensate for differences in the surrounding atmosphere and provide for consistent particle size it may be desirable to include a means for adding energy to the surrounding atmosphere so as to minimize, to the extent possible, the effect of water vapor in the surrounding atmosphere. Alternatively, it may desirable to saturate the surrounding atmosphere with water vapor. Either method could provide for consistency in the size of particles delivered to the patient. Means for carrying out the dynamic particle size adjustment are disclosed within U.S. patent application Ser. No. 08/313,461 filed Sep. 27, 1994, entitled "Dynamic Particle Size Control for Aerosolized Drug Delivery" which application is incorporated herein by reference in its entirety and incorporated specifically to disclose means for adjusting aerosolized particle size to obtain consistency regardless of the surrounding atmosphere.

Dosing Aerosolized Drugs

Based on the above, it will be understood that the dosing or amount of analgesic drug actually released from the device can be changed based on the most immediately prior monitoring event wherein the inspiratory flow of a patient's inhalation is measured.

Variations in doses are calculated by monitoring the effect of respiratory rate in response to known amounts of analgesic drug released from the device. If the response in decreasing the patient's respiratory rate is greater than with previous readings, then the dosage is decreased or the minimum dosing interval is increased. If the response in decreasing respiratory rate is less than with previous readings, then the dosing amount is increased or the minimum dosing interval is decreased. The increases and decreases are gradual and are preferably based on averages (of 10 or more readings of respiratory rates after 10 or more dosing events) and not a single dosing event and monitoring event with respect to respiratory rates. The present invention can record dosing events and respiratory rates over time, calculate averages and deduce preferred changes in administration of analgesic drug.

One of the important features and advantages of the present invention is that the microprocessor can be programmed to take two different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 micrograms of a narcotic within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 micrograms of a narcotic during an hour which could only be released in amounts of 25 micrograms with each release being separated by a minimum of five minutes.

The dosing program can be designed with some flexibility. For example, if the patient normally requires 25 mg per day of analgesic drug, the microprocessor of the inhalation device can be programmed to prevent further release of the valve after 35 mg have been administered within a given day. Setting a slightly higher limit would allow for the patient to administer additional analgesic drug, if needed, due to a higher degree of pain and/or account for misdelivery of analgesic drug such as due to coughing or sneezing during an attempted delivery.

The ability to prevent overdosing is a characteristic of the device due to the ability of the device to monitor the amount of analgesic drug released and calculate the approximate amount of analgesic drug delivered to the patient based on monitoring given events such as the respiratory rate. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of analgesic drug merely by the manual actuation of a button to fire a burst of analgesic drug into the air or a container.

The microprocessor will also include a timing device. The timing device can be electrically connected with visual display signals as well as audio alarm signals. Using the timing device, the microprocessor can be programmed so as to allow for a visual or audio signal to be sent when the patient would be normally expected to administer analgesic drug. In addition to indicating the time of administration (preferably by audio signal), the device can indicate the amount of analgesic drug which should be administered by providing a visual display. For example, the audio alarm could sound alerting the patient that analgesic drug should be administered. At the same time, the visual display could indicate "50 µg" as the amount of analgesic drug to be administered. At this point, a monitoring event could take place. After completion of the monitoring event, administration would proceed and the visual display would continually indicate the remaining amount of analgesic drug which should be administered. After the predetermined dose of 50 µg had been administered, the visual display would indicate that the dosing event had ended. If the patient did not complete the dosing event by administering the stated amount of analgesic drug, the patient would be reminded of such by the initiation of another audio signal, followed by a visual display instructing the patient to continue administration.

Additional information regarding dosing with analgesic drug via injection can be found within Anesthesa, (most recent edition) edited by Miller, and published by Churchill and Livingston and Harrison's—Principles of Internal Medicine (most recent edition) published by McGraw Hill Book Company, New York, incorporated herein by reference to disclose conventional information regarding dosing analgesic drug via injection.

Supplemental Treatment Methodology

Patients suffering from pain may be treated solely with analgesic drug as indicated above, i.e. by intrapulmonary delivery. However, it is possible to treat such patients with a combination of analgesic drug(s) provided by other means of administration. More specifically, a patient can be provided with a basal level of analgesic drug by a means such as transdermal administration and/or oral administration. This basal level of drug will be sufficient to control the pain of the patient during normal circumstances. However, when the pain becomes more intense, the patient can quickly obtain relief by the intrapulmonary administration of an analgesic drug such as sufentanil using the device and methodology of the present invention. The intrapulmonary delivery of analgesic drug provides a pulsalite rate increase over the normal basal rate level maintained by the oral or transdermal administration. The use of the intrapulmonary administration of analgesic drug via the present invention is particularly desirable in that the effects of the drug are felt almost immediately. Such an immediate effect cannot be obtained using oral and/or transdermal administration means.

Fentanyl is available for administration by a transdermal delivery system in the form of a skin patch [Duragesic™ (fentanyl transdermal system) package insert, Janssen Pharmaceutica, Piscataway, N.J. 08855, January–June 1991].

In addition to administering narcotics by transdermal administration it is possible to administer the drugs by other means such as by injection and/or orally. In accordance with the present invention a preferred supplemental means of administration is oral in that oral administration can be carried out on an out-patient basis. Thus, the method of the invention may be carried out by administering a long acting orally effective narcotic drug. The oral drug is preferably given in amount so as to maintain a relatively low level of narcotic within the circulatory system which is sufficient to control pain during periods when the pain is less severe. However, this low level of drug to blood ratio must be raised in order to control more severe pain and such can be accomplished by the interpulmonary administration of narcotic using the present invention.

Based on the above, it will be understood by those skilled in the art that a plurality of different treatments and means of administration can be used to treat a single patient. For example, a patient can be simultaneously treated with analgesic drug by injection, analgesic drug via intrapulmonary administration in accordance with the present invention, and drugs, which are orally administered. Should such prove to be ineffective for whatever reason, such as breathing difficulties (not related to the administration of the analgesic drug), such could be supplemented by administration via injection.

Treating Overdoses with Narcotic Antagonist

The methodologies of the present invention can be carried out using any type of analgesic drug, although they are preferably carried out using potent narcotic such as fentanyl and morphine. The biochemical mechanism of action of such narcotics is known. Further, it is known that the narcotic effect can be blocked by the administration of a narcotic antagonist such as naloxone. The devices and methodology disclosed and described herein may be used to deliver narcotic antagonists such as naloxone.

Controlled Access of Toxic Drugs

Although the primary purpose of the present invention is to provide a device and methodology for controlling access to narcotic drugs the device and methodology can also be used to control access to certain toxic drugs. This is particularly important when the drugs might be brought into contact with children. For example, drugs such as insulin can be delivered using methodology such as that disclosed herein. For example, see U.S. patent application Ser. No. 08/011,281 filed Jan. 29, 1993, entitled "Method of Administration of Insulin" incorporated herein by reference. In that the administration of insulin to a patient not in need of insulin could be toxic, the electronic locking devices of the present invention could be used to prevent delivery of the insulin or any toxic drug to unauthorized users.

Treatment of Drug Addicts

Attempts at treating drug addicts can involve the administration of certain drugs to the patient. However, since the drugs being administered are controlled substances the treatment programs often require that the patient being treated return to a drug treatment clinic on a daily basis. In part because it is difficult to convince such patients to continue treatment when they must return to a specific clinic on a daily basis, the treatment programs often fail. By using the methodology and devices of the present invention it is possible to provide a drug addict being treated with a device which includes a large number of doses of drug for treatment. The device could be programmed so that it could not be accessed by others and can be programmed so that it will not release more than a preprogrammed amount of drug during a preprogrammed amount of time.

Delivery Device

There are two preferred types of devices which can be used with the present invention. In general, one type uses a low boiling point propellant and the other uses aqueous formulations. The devices which use low boiling point propellants are shown in FIGS. 1–4 and an embodiment of a device which uses aqueous formulations is shown in FIG.

10. Regardless of which type is used the device is a hand-held, portable device which is comprised of (a) a means for separately measuring and analyzing the inspiratory flow rate and inspiratory volume of a patient and (b) a means for automatically releasing a measured amount of a narcotic into the inspiratory flow path of a patient, e.g. an automatic valve actuation means or mechanism for moving formulation through a porous membrane. In order to use the device, the device must be "loaded", i.e. connected to (c) a source of pain relieving drug which, in general, is a potent narcotic drug in water or in a low boiling point propellant. The entire device is light weight (less than 1 kg loaded) and portable.

A formulation of an analgesic drug in a low boiling point propellant is typically contained in a pressurized canister which is connectable to the "unloaded" device, i.e., the device without the container. Particularly preferred narcotic formulations of this type are disclosed in U.S. patent application Ser. No. 08/242,223 filed Jun. 16, 1993 which is incorporated herein by reference to disclose such formulations. When the container of propellant and analgesic drug is connected to the device, the container will include a valve opening at one end which opening is seated into a flow path within the device. The device preferably includes a mouth piece at the end of the flow path, and the patient inhales from the mouth piece which causes an inspiratory flow to be measured within the flow path. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means. When the actuation means is signaled, it releases a valve allowing analgesic drug and propellant to escape into the inspiratory flow path of the device and ultimately into the patient's lungs. After being released, the drug and propellant will preferably pass through a nozzle prior to entering the inspiratory flow path of the device and thereafter the lungs of the patient.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug. The high degree of dosing repeatability needed to deliver narcotics may be obtained merely by measuring and releasing at the same measure flow rate and volume for each release of drug. Further, the device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time.

FIG. 1 shows a cross-sectional view of a hand-held, portable, electronic breath-actuated inhaler device which can be used in connection with the present invention. The device is shown with a holder 1 having cylindrical side walls and a removable cap. The holder 1 is "loaded" in that it includes the pressurized canister 3. The canister 3 includes a non-metering valve 5 which is held down in the open position when the cap 2 is screwed down, thus setting the valve 5 into a seat 6 which is in connection with a flow path 8.

A formulation 4 comprised of a narcotic such as sufentanil or fentanyl and a suitable propellant, such as a low boiling point propellant, is contained within the pressurized canister 3. Propellant and narcotic drug are released from the canister 3 via the electrically controlled solenoid 7. In that the valve 5 of the canister is continuously open, another valve, contained within solenoid 7, facilitates the release of the drug. When the solenoid 7 allows release of propellant and drug, the propellant and drug flows through the flow path 8 and then through the solenoid actuated valve 9 into the flow path 10, out through the nozzle 13 and then into the inspiratory flow path 11 surrounded by walls 12.

It is important to note that a variety of devices can be used in order to carry out the pain management delivery methodology of the present invention. However, the device must be capable of allowing the release of a metered amount of analgesic drug based on pre-programmed criteria relating to flow rate and volume. These measurements may be made mechanically but are preferable electronic and are readable by the microprocessor 22. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 22, containing read only memory which in turn contains the pre-programmed information, is plugged into the device. For each of these three embodiments, changing the programming of the memory device readable by microprocessor 22 will radically change the behavior of the device by causing microprocessor 22 to be programmed in a different manner. As regards the present invention, the non-volatile memory contains information relevant only to the administration of a specific analgesic drug such as fentanyl. Microprocessor 22 sends signals to solenoid 7 which determines the amount of drug delivered into the inspiratory flow path. Further, microprocessor 22 keeps a record of all drug dosing times and amounts using a read/write non-volatile memory which is in turn readable by an external device. The formulation 4 contained within canister 3 is released into the atmosphere ultimately via nozzle 13 which opens into inspiratory flow path 11. It is at this point that the low boiling point propellant within formulation 4 flashes, i.e. rapidly evaporates, thus providing particles of analgesic drug in an aerosol which is introduced into the mouth and ultimately into the lungs of the patient. In order to allow for ease of use, it is possible to form inspiratory flow path 11 into a mouth piece which can be specifically designed to fit the mouth of a particular patient using the device.

The solenoid 7, and associated valve 9, flow paths 8 and 10, as well as nozzle 13 make up the aerosol delivery system 14 shown by the dotted lines within FIG. 1. The system 14 is in connection with the flow sensor 15 which is capable of measuring a flow rate of about 0 to about 300 liters per minute. The flow sensor 15 includes screens 16, 17 and 18 which are positioned approximately ¼" apart from each other. Tubes 19 and 20 open to the area between the screens 16, 17 and 18 with the tubes 19 and 20 being connected to a conventional differential pressure transducer 21. When the user draws air through inspiratory flow path 11, air is passed through the screens 16, 17 and 18 and the air flow can be measured by the differential air pressure transducer 21. The flow sensor 15 is in connection with the aerosol delivery system 14, and when a threshold value of air flow is reached, the aerosol delivery system 14 allows the release of formulation 4 so that a controlled amount of analgesic drug is delivered to the patient. Solenoid 7 is connected to a microprocessor 22 via an electrical connection. The details of the microprocessor and the details of other drug delivery devices which might be used in connection with the present invention are described and disclosed within U.S. patent application Ser. No. 07/664,758, filed on Mar. 5, 1991 entitled "Delivery of Aerosol Medications for Inspiration" which application is incorporated in its entirety herein by reference, and it is specifically incorporated in order to describe and disclose devices as shown within FIG. 1 and the microprocessor and program technology used therewith.

Figure 2:
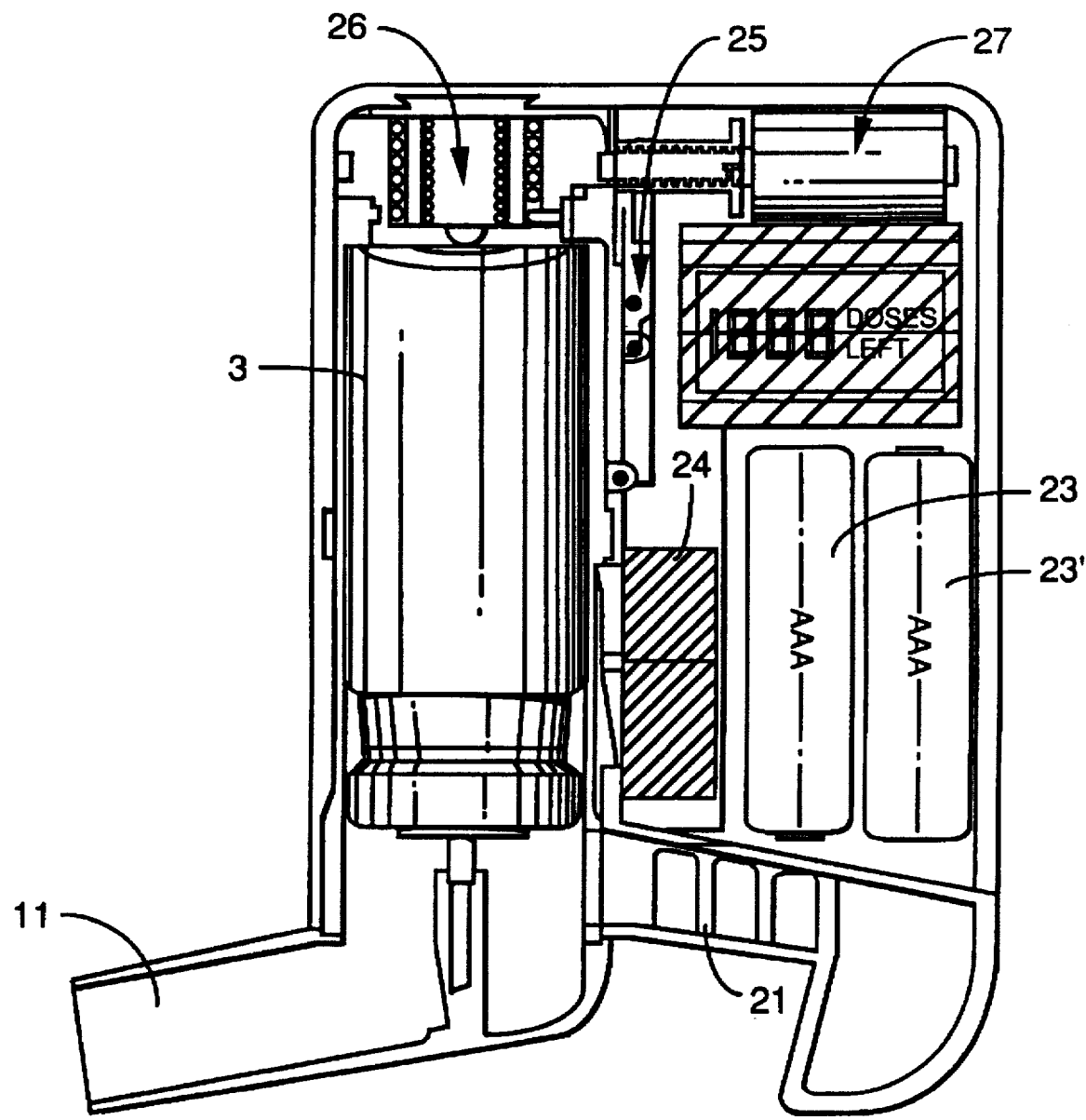

A cross-sectional view of yet another (and more preferred) embodiment of the hand-held, electronic, breath-actuated inhaler device of the invention is shown in FIG. 2. The device of FIG. 2 shows all of the components present within the single hand-held, portable device, i.e. the power source not shown in FIG. 1 is shown in the device in FIG. 2. Like the device shown within FIG. 1, the device of FIG. 2 includes a canister 3 which includes a canister valve 5. However, unlike the device of FIG. 1, the device of FIG. 2 does not have the valve continuously open but allows a valve 5 connected to the canister 3 to be opened by the mechanical force generated by a valve actuation mechanism 26 which is a motor driven, mechanical mechanism powered by a power source such as batteries 23 and 23'. However, like the device shown within FIG. 1, the patient inhales through inspiratory flow path 11 which can form a mouth piece in order to obtain a metering event using the differential pressure transducer 21. Further, when the inspiratory flow meets a threshold of a pre-programmed criteria, the microprocessor 24 sends a signal to an actuator release mechanism 25 which actuates the actuation mechanism 26 forcing canister 3 downward so that canister valve 5 releases formulation into the inspiratory flow path 11. Further details regarding the device of FIG. 2 are described within co-pending U.S. patent application entitled "An Automatic Aerosol Medication Delivery System and Methods", filed on Jan. 29, 1993 as U.S. Ser. No. 08/002,507, which application is incorporated herein by reference in its entirety and specifically incorporated in order to describe and disclose devices as shown within FIG. 2 and the microprocessor and program technology used therewith.

Microprocessor 24 of FIG. 2 includes an external non-volatile read/write memory subsystem, peripheral devices to support this memory system, reset circuit, a clock oscillator, a real time clock module, a data acquisition subsystem and an LCD annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of analgesic drug to a patient upon actuation. Adjustments can be made in the program so that when the patient's inspiratory flow profile is changed such is taken into consideration. This can be done by allowing the patient to inhale through the device as a test in order to measure air flow with preferred drug delivery points determined based on the results of several inhalations by each particular patient. This process can be readily repeated when the inspiratory flow profile is changed for whatever reason, e.g. abdominal incisional pain resulting in low tidal volumes. Determination of optimal drug delivery points in the inspiratory flow can be done at each dosing event, daily, weekly, or with the replacement of a new canister in the device.

The microprocessor of the present invention, along with its associated peripheral devices, can be programmed so as to prevent the release of drug from the canister from occurring more than a given number of times within a given period of time. This feature makes it possible to prevent overdosing the patient with a potent narcotic. The overdose prevention feature can be particularly designed with each individual patient in mind or designed with particular groups of patients in mind. For example, the microprocessor can be programmed so as to prevent the release of more than approximately 200 µg of fentanyl per day when the patient is normally dosed with approximately 100 µg of fentanyl per day. The systems can also be designed so that only a given amount of a particular analgesic drug is provided at a given dosing event. For example, the system can be designed so that only approximately 100 µg of fentanyl is given in a given 15-minute period over which the patient will make approximately 10 inhalations with 10 µg of fentanyl being delivered with each inhalation. By providing this feature, greater assurances are obtained with respect to delivering the analgesic drug gradually over time and thereby providing pain management without overdosing the patient.

Access to a drug in the device is controlled by electronically interconnecting the microprocessor of the drug delivery device just described (FIG. 2) to an electronic lock means which can be accessed only with an electronic key device. The microprocessor of the drug delivery device is programmed to not release drug if it does not receive a signal transmitted to it by an electronic lock means coupled to a matching coded electronic key means worn by the intended user. Such a system prevents abuse by unauthorized users.

Figure 11:
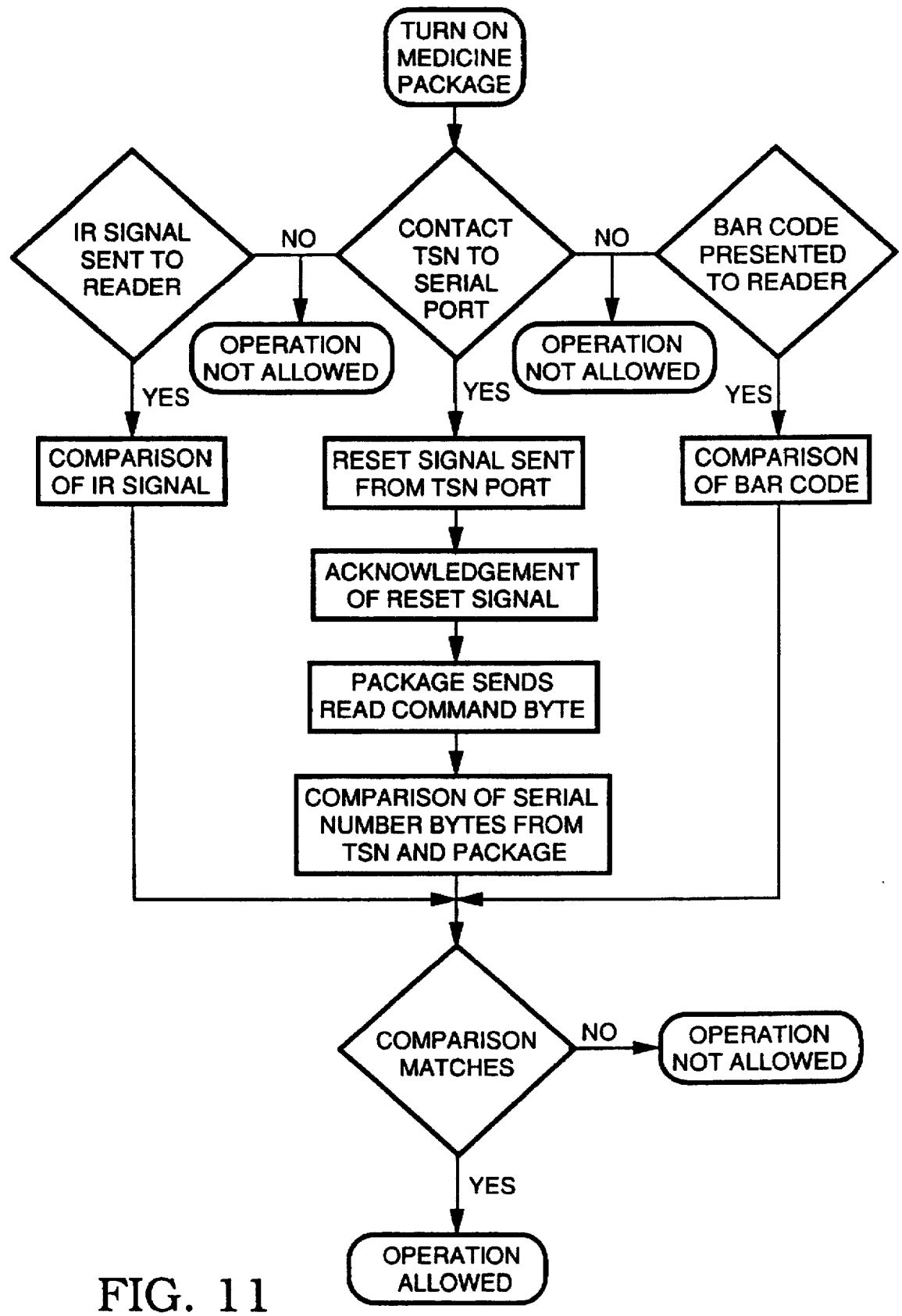

An electronic lock and key mechanism such as the TSN described in FIG. 11 has an electrical interface comprised of a metallic cylindrical housing which holds the TSN and has two contacts. The front surface of the housing acts as the data I/O line into the device, while the back and side surfaces act as the signal ground. The TSN I/O line is bi-directional and the line is preferably connected to an open-drain or tri-state driver. The TSN I/O line is preferably pulled up with a 5K resistor. The idle state for this line is high; during idle periods, the TSN draws power from the host via this signal.

The microprocessor of the lock means is reset prior to reading data from the TSN (see FIG. 11). The microprocessor initiates the reset by driving the I/O line low preferably for at least 480 µs, then releasing the line (i.e., allowing the line to return to its default high level). The TSN will acknowledge the reset by waiting approximately at least 15 µs and not more than approximately 60 µs. Then driving this line low for at least approximately 60 µs and not more that approximately 240 µs, then releasing the line. The microprocessor of the lock means is preferably programmed to allow at least approximately 480 µs for the TSN to complete this acknowledgement.

After the TSN has been reset, the command byte, which equals ϕF hexadecimal, is written into the TSN before its ROM data may be read. This command is written into the TSN one bit at a time, least significant bit first.

Figure 10:
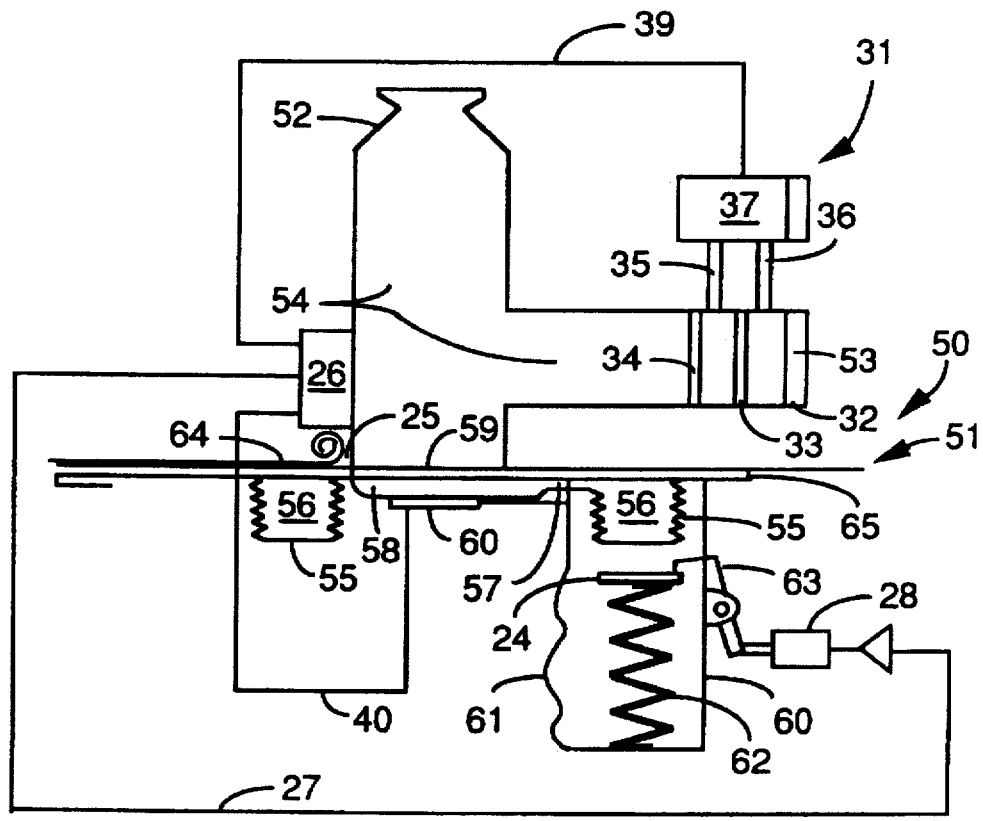

Preferably, a write cycle is initiated by the microprocessor of the lock means by bringing the I/O line low for approximately 1–15 µs (see FIG. 10). If the microprocessor of the lock means is writing a "0", it continues to hold this line low for a total low time of approximately 60–120 µs. The TSN samples this line approximately 15–60 µs after the start of the low-going pulse. After the "0" has been written, the host must release this line for at least approximately 1 µs to allow the TSN to draw power from the line.

If a "1" is being written to the TSN, the microprocessor of the lock means releases the I/O line after generating its approximately 1–15 µs pulse; the pull-up resistor then pulls this signal high. As before, the TSN samples this line approximately 15–60 µs after the start of the low-going pulse, so this write period should be a minimum of approximately 60 µs in duration. After the "1" has been written, the microprocessor of the lock means preferably waits at least approximately 1 µs before beginning the next bit transaction.

After the command byte, which equals φF hexadecimal, has been sent to the TSN, its ROM data may be read (see FIG. 11). The TSN will first transmit its family code (for example, φ1 hexadecimal), followed by a unique 48 bit serial number, followed by a single CRC byte encompassing the family and serial number data. All data are preferably transmitted by the least significant bit first.

A read cycle is initiated by the microprocessor of the lock means by driving the I/O line low for approximately 1–15 µs, then releasing it. If the TSN data bit is a "0", the TSN will drive this line low for approximately 15–60 µs after the start of the low-going pulse, after which it will release the line. If the TSN data bit is a "1", the TSN will leave the I/O line unaffected.

Preferably, the lock means microprocessor's low going pulse is as close to 1 µs as possible to maximize its valid read window. The lock means microprocessor preferably samples the signal no more than 15 µs after initiating the read cycle. The entire read period should be at least 60 µs long, after which the lock means microprocessor preferably waits at least approximately 1 µs before beginning the next bit transaction.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. The devices of FIGS. 1 and 2 have been put forth in connection with devices which use a low boiling point propellant and preferably use that propellant in combination with a suspension formulation which includes the dry powdered analgesic drug within the low-boiling-point propellant. Those skilled in the art will readily recognize that such devices can be used for administering a solution of analgesic drug within the low-boiling-point propellant. However, those skilled in the art will also readily recognize that different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

Aqueous System Device

The device of FIGS. 1 and 2 can be used to deliver a formulation of narcotic drug and low boiling point propellant. The system shown in FIG. 10 is used to deliver a formulation of analgesic drug (e.g. narcotics) in a carrier of water and/or ethanol. An embodiment of such a device will now be described in detail.

The device 50 shown in FIG. 10 is loaded with a disposable package 51. To use the device 50 a patient (not shown) inhales air from the mouthpiece 52. The air drawn in through the opening 53 and flows through the flow path 54. The package 51 is comprised of a plurality of containers 55. Each container 55 includes a drug formulation 56 and is in fluid connection via a channel 57 with the cavity 58. The cavity 58 is covered by the porous membrane 59. A vibration device 60 may be positioned directly below the cavity 58.

The device 50 is a hand-held, portable device which is comprised of (a) a device for holding a disposable package with at least one but preferably a number of drug containers, (b) a mechanical mechanism (e.g. piston or vibrator for moving the contents of a container (on the package) through a porous membrane (c) a device for separately measuring the inspiratory flow rate and inspiratory volume of a patient, and (d) a switch for automatically releasing or firing the mechanical means after the inspiratory flow rate and/or volume reaches a predetermined point. If the device is electronic it also includes (e) a source of power.

The device for holding the disposable package may be nothing more than a narrow opening created between two outwardly extending bars or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to roller(s) so that when they are rotated, they move the package from one container to the next. A power source driving the roller(s) can be programmed to rotate the rollers only enough to move the package from one container to the next. In order to use the device, the device must be "loaded," i.e. connected to a package which includes drug dosage units having liquid, flowable formulations of pharmaceutically active drug therein. The entire device is self-contained, light weight (less than 1 kg preferably less than 0.5 kg loaded) and portable.

FIG. 10 shows a cross-sectional view of a hand held, self-contained, portable, breath-actuated inhaler device 50 which can be used in the method of the present invention. The device 50 is shown with a holder 60 having cylindrical side walls and a hand grip 61. The holder 2 is "loaded" in that it includes a package 51. The package 51 includes a plurality of containers 56 connected by a connecting member 65.

The embodiment shown in FIG. 10 is a simple version of a device 50 which may be manually actuated and loaded. More specifically, the spring 62 may be compressed by the user until it is forced down below the actuation mechanism 63. When the user pushes the actuation mechanism 63 the spring 62 is released and the mechanical means in the form of a plate 24 is forced upward against a container 56. When the container 56 is compressed its contents are forced out through the channel 57 and membrane 59 and aerosolized. Another container 56 shown to the left is unused. A top cover sheet 64 has been peeled away from the top of the membrane 59 by a peeling means 25. The embodiment of FIG. 10 could provide the same results as a conventional metered dose inhaler. However, the device of FIG. 10 would not require the use of low boiling point propellants such as low boiling point fluorocarbons. Numerous additional features and advantages of the present invention can be obtained by utilizing the monitoring and electronic components described below.

The device must be capable of aerosolizing drug formulation in a container and preferably does such based on pre-programmed criteria which are readable by the microprocessor 26. The details of the microprocessor 26 and the details of other drug delivery devices which include a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and is specifically incorporated in order to describe and disclose the microprocessor and program technology used therewith. The use of such a microprocessor with a drug delivery device is disclosed in our earlier filed U.S. patent application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the preprogrammed information, is plugged into the device. For each of these three embodiments, changing the programming of the memory device readable by microprocessor 26 will radically change the behavior of the device by causing microprocessor 26 to be programmed in a different manner. This is done to accommodate different analgesic drugs.

Microprocessor 26 sends signals via electrical connection 27 to electrical actuation device 28 which actuates the means 63 which fires the mechanical plate 24 forcing drug formulation in a container 56 to be aerosolized so that an amount of aerosolized drug is delivered into the inspiratory flow path 54. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 51. The recorded information can be read later by the care-giver to determine the effectiveness of the treatment. In order to allow for ease of use, it is possible to surround the inspiratory flow path 54 with a mouth piece 52.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. The flow sensor 31 includes screens 32, 33 and 34 which are positioned approximately ¼" apart from each other.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 54, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 63 releasing the plate 24 which forces the release of formulation from a container 56 so that a controlled amount of drug is delivered to the patient. The microprocessor 26 is also connected via connector 40 to an optionally present vibrating device 60 which may be activated.

Vibration Device

The ultrasonic vibrations are preferably at right angles to the plane of the membrane 14 and can be obtained by the use of a piezoelectric ceramic crystal or other suitable vibration device 60. The vibrating device 60 in the form of a piezoelectric crystal may be connected to the porous membrane 59 by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 59 allowing for maximum use of the energy towards aerosolizing the liquid formulation 56. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 800 kilohertz (Khz) to about 4,000 kilohertz. The power output required depends upon the amount of liquid being nebulized per unit of time and the area and porosity of the polycarbonate membrane used for producing the drug dosage unit and/or the efficiency of the connection.

Vibration is applied while the formulation 56 is being forced from the pores of the polycarbonate membrane 59. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about one to 200 psi, preferably 50 to 125 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores. In general, the present invention does not create effective aerosols if the viscosity of the liquid is greater than about 50 centipoises.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air or any other gas is forced through openings as the aerosol is forced out of the porous membrane. Accordingly, an air flow is created toward the patient and away from the nozzle opening which carries the formed particles along and aids in preventing their collision with each other. The amount of gas forced from the openings will vary depending upon the amount of aerosol being formed. However, the amount of gas is generally five to two hundred times the volume of the liquid formulation within the container. Further, the flow velocity of the gas is generally about equal to the flow velocity of the aerosolized particles being forced from the nozzle. The shape of the container opening, the shape of the membrane covering that opening, as well as the positioning and angling of the gas flow and particle flow can be designed to aid in preventing particle collision. When the two flow paths are substantially parallel, it is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangle. Using such a configuration makes it possible to better utilize the air flow relative to all of the particles being forced form the container. When a circular opening is used, particles which are towards the center of the circle may not be carried along by the air being forced from the openings and will collide with each other. The elongate rectangle could be formed in a circle, thereby providing an annular opening and air could be forced outward from the outer and inner edges of the circle formed. Further details regarding such are described in U.S. patent application Ser. No. 08/247,012 filed May 20, 1994 which is incorporated herein by reference to disclose and describe such.

Security Features

In that narcotic drugs are subject to drug abuse it is desirable to design devices and methodology so as to hinder abuse to the extent possible. The methodology and devices of the present invention do so in an number of specific ways.

The device shown within FIG. 2 is designed to be reusable. More specifically, the drug delivery device can be "loaded" with a cassette of the type shown within either of FIGS. 3 and 4. The cassette is comprised of an outer cover 30, a canister 3 and top nozzle piece 31. The components are shown in a disassembled state in FIG. 3. A different embodiment of such components are shown in an assembled state within FIG. 4.

Figures 3, 4:
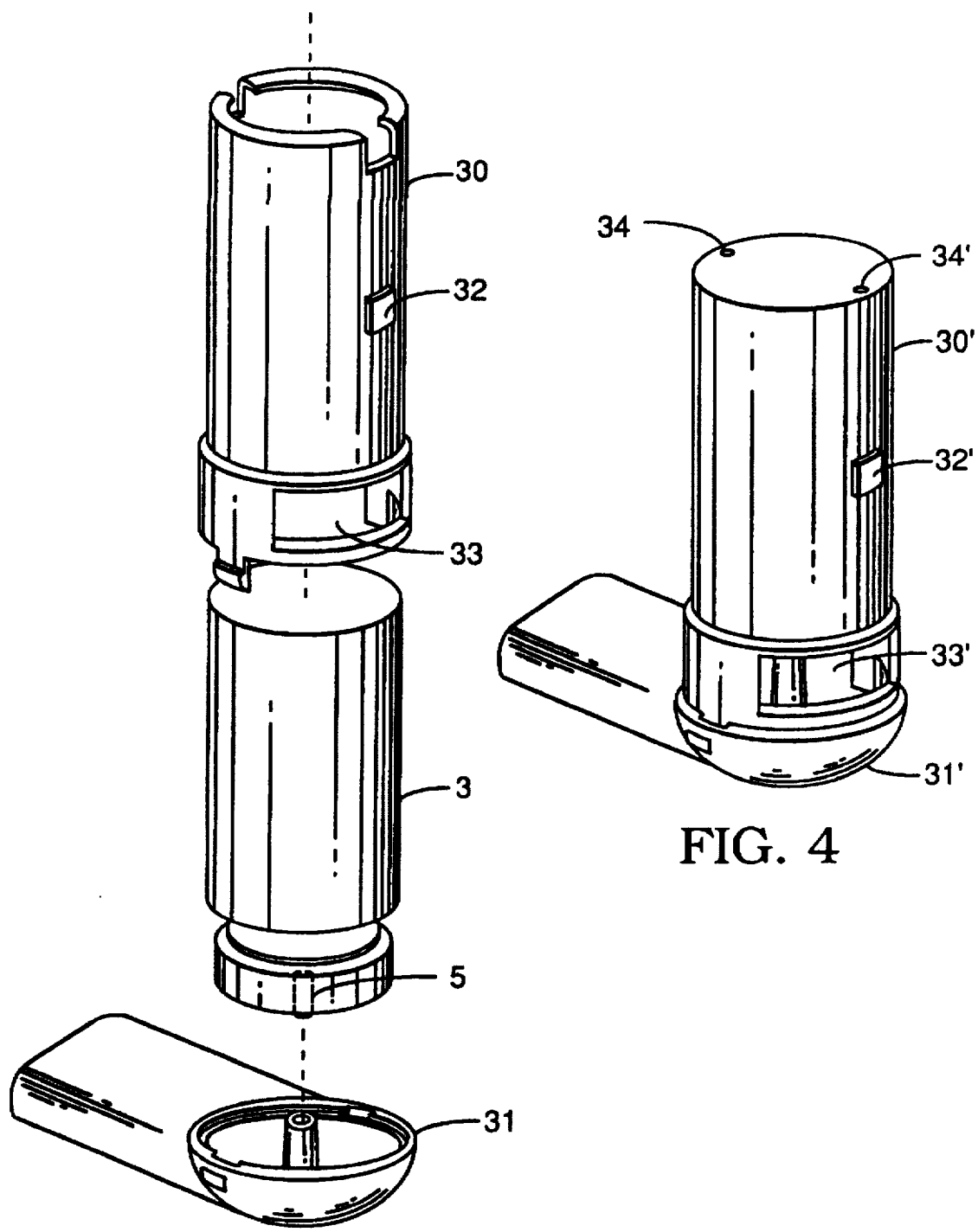

In essence, the cassette shown in FIG. 3 is somewhat less secure than the cassette shown within FIG. 4. As indicated, the top portion of the cover 30 is open within FIG. 3. This allows one to force the canister 3 downward and open the valve 5 to allow release of drug. However, in the embodiment shown in FIG. 4, there is no general opening but only two small openings 34 and 34'. Using the embodiment shown in FIG. 3, the cassette is loaded within the device shown in FIG. 2 and a motor driven piston forces the bottom of the canister 3 downward actuating the valve 5 to an open position. In accordance with the embodiment shown within FIG. 4, a two-pronged fork device is positioned over the end portion of the cover 30'. Each prong of the fork protrudes through an opening 34 and 34' allowing the canister 3 to be forced downward so that the valve 5 can be opened. It should be pointed out that when the cover 30 is attached to the top nozzle piece 31, they can be sealed together using a fast-acting glue or any appropriate means making it impossible to separate the components.

In that the narcotic drug is contained within the canister 3 with a low boiling point propellant it is extremely difficult to open the canister without losing all of the contents. Accordingly, the contents of the canister can generally be obtained only by including the canister within components 30 and 31 and attaching such to the device shown within FIG. 2.

The following description is provided with respect to FIG. 3 and the component shown therein, but is equally applicable with respect to FIG. 4 and the component shown therein. The cover 30 can have protuberances such as the protuberance 32 and openings such as the opening 33 thereon. These openings and protuberances can serve as a type of lock and key mechanism which is interactable with receiving protuberances and openings in the device shown in FIG. 2. Accordingly, unless the cover 30 includes the correct openings and protuberances in the correct position the cover will not fit into the device shown in FIG. 2 and cannot be operated. The body of the device as shown within FIG. 2 is designed so as to be capable of receiving the openings and protuberances on the cover 30. Although devices such as those shown within FIG. 2 might be utilized to dispense a variety of different types of drugs the physical configuration of the device is specific with respect to certain drugs and is particularly specific with respect to narcotic drugs. Thus, the cover 30 and receiving body portion on the device of FIG. 2 are designed so that they can be integrated but are also designed so that they will not integrate with other devices not specific for the delivery of narcotic drugs. Thus, as a first layer of security the device and methodology of the present invention provides for a physical lock and key interaction.

As a second line of defense against misuse of drugs, it is possible to design the components 31 and 32 and/or the device shown in FIG. 2 so as to receive a signal from a remote transmitter which is worn by the patient for which the drug was prescribed by the prescribing physician. By designing the device in this manner no drug can be released from the device unless the device is in close proximity to the intended user of the device.

A more preferred embodiment of a controlled access device is described herein as an electronic key device such as a Touch Serial Number (Dallas Semiconductor) device. Using this electronic key access to a drug in a delivery device such as an aerosol device disclosed herein is restricted to those patients possessing a code-matching TSN that is provided by the patients physician or other health professional upon prescription of the drug and the delivery device. The TSN is preferably worn by the intended user (the patient) on a bracelet or badge for convenient use with the delivery device. Further, the TSN is unavailable to unintended users to prevent unintended users from accessing the drug (such a legally controlled narcotic or other toxic drug).

It will, of course, be apparent to those skilled in the art that a combination of all or any of the above security features can be used. Further, the transmitting and receiving signals can be by any means of signalling and need not be limited to radio signals and thus could include infrared and other types of signals. Further, other interlocking mechanisms with more complex physical shapes could be readily devised in order to enhance the security of the device.

As indicated above, the valve actuation means can be electronically prevented from allowing the release of valves. As further indicated above, this is generally done for purposes of security. However, such can also be implemented in order to prevent accidental overdosing by a given patient. For example, the monitoring components of the invention can be designed so as to read the patients respiratory rate. If the respiratory rate is below a given value assigned to the particular patient then the electronics can prevent the release of any drug from the device. It is well known that respiratory rates slow when large amounts of narcotics are administered to a patient. Accordingly, if the patients respiratory rate has been slowed to a dangerously low rate it is important to prevent further administration of drug to the patient.

Lock and Key

The present invention includes methodology for dispensing aerosolized drugs and a device which dispenses aerosolized drugs when activated. The drug dispensing device may be deactivated by a "lock" which lock may be of a variety of different types and may be "unlocked" by a variety of different types of keys (shown schematically in FIG. 11).

The "lock" on the device may be an internal microprocessor of the device. A "key" such as a TSN activates the lock by sending a unique electronic code to the internal microprocessor. After verification of the unique code, the prevention device is activated, allowing drug delivery. Receipt of no electronic code, or of a non-matching code, would not "unlock" the prevention device.

Alternatively, the lock on the device may be a bar code reader. Activation of the prevention device will occur only if the bar code reader is presented with the correct, unique bar code (the key). Upon receipt of the appropriate bar code, the bar code reader sends a signal which activates a microprocessor control device which essentially turns the drug dispensing device on so that it may be used to dispense aerosolized drug.

In another embodiment, the lock is a device which receives infrared signals and is activated by the receipt of a unique infrared signal (the key). The "infrared key" sends a signal to the microprocessor so that the device is turned on and can be used for the dispensing of a predetermined amount of drug.

Regardless of the lock/key combination employed in the delivery device, the device will deactivate after a predetermined amount of drug has been dispensed. The device may be programmed so that it cannot be reactivated for a given period of time even if it does receive the required information from an appropriate key. Those skilled in the art will contemplate a variety of different types of "lock" and "key" combinations which could be used in order to prevent access to and/or activation of a drug dispensing device which creates aerosolized drug formulation for inhalation by a patient.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

We claim:

1. A hand-held, portable, self-contained aerosol drug delivery system comprising:

a disposable container having therein an analgesic drug formulation and a nozzle thereon through which the formulation is aerosolized for delivery to the patient;

a prevention device which prevents and allows access to the analgesic drug formulation until the device is activated by an electronic signal;

a lock which activates the prevention device upon receipt of a unique code;

a drug dispensing component which aerosolizes the formulation for inhalation; and a key which sends a unique code to the lock, wherein the key is external to the body of the device.

2. The system of claim 1, wherein the key is a readable bar code and the lock is a bar code reader which prevents activation of the prevention device until the correct bar code is read.

3. The system of claim 1, wherein the key is an infrared sending device and the lock is an infrared receiving device which prevents activation of the prevention device until the infrared signal is received from the key.

4. The method of claim 1, wherein the key is an electronically encoded key and the lock is a means for reading the electronically coded key and preventing activation of the prevention device until the electronic code of the key is read.

5. The system of claim 1, wherein the container is a pressurized container having therein a narcotic drug and a low-boiling point propellant held in the container under pressure.

6. The system of claim 5, wherein the prevention device is a valve locking means and the lock is a signal receiving means and the key is a signal transmitting means, wherein the signal receiving means prevents actuation of the valve for releasing analgesic drug until receiving a signal from the signal transmitting means.

7. The device as claimed in claim 6, wherein the signal transmitting means sends an encoded radio frequency signal and the signal receiving means receives the encoded radio frequency signal.

8. The drug dispensing system of claim 6, wherein the valve locking means is maintained in a state so as to lock the valve until the lock receives a signal from a respiratory rate monitoring means indicating that a measured respiratory rate is above a predetermined minimum respiratory rate.

9. The system of claim 1, wherein the container is a container of a unit dose of narcotic drug in a liquid carrier which container includes a wall comprised of a porous membrane which membrane includes pores having a diameter in the range of 0.25 to about 2.5 microns.

* * * * *